(12) United States Patent
Willett et al.

(10) Patent No.: US 9,296,800 B2
(45) Date of Patent: Mar. 29, 2016

(54) SERUM AMYLOID P DERIVATIVES AND THEIR PREPARATION AND USE

(75) Inventors: W. Scott Willett, Doylestown, PA (US); Richard J. Caimi, Maple Glen, PA (US)

(73) Assignee: Promedior, Inc., Lexington, MA (US)

( * ) Notice: Subject to any disclaimer, the term of this patent is extended or adjusted under 35 U.S.C. 154(b) by 722 days.

(21) Appl. No.: 12/794,132

(22) Filed: Jun. 4, 2010

(65) Prior Publication Data

US 2010/0317596 A1    Dec. 16, 2010

Related U.S. Application Data

(60) Provisional application No. 61/217,931, filed on Jun. 4, 2009.

(51) Int. Cl.
*C07K 14/47* (2006.01)
*A61K 38/00* (2006.01)

(52) U.S. Cl.
CPC .......... *C07K 14/47* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,233,969 A | 11/1980 | Lock et al. | |
| 4,556,056 A | 12/1985 | Fischer et al. | |
| 4,782,014 A | 11/1988 | Serban et al. | |
| 5,092,876 A | 3/1992 | Dhawan et al. | |
| 5,591,709 A | 1/1997 | Lindenbaum | |
| 5,654,186 A | 8/1997 | Cerami et al. | |
| 5,698,589 A | 12/1997 | Allen | |
| 5,750,345 A | 5/1998 | Bowie | |
| 5,804,446 A | 9/1998 | Cerami et al. | |
| 5,846,796 A | 12/1998 | Cerami et al. | |
| 5,989,811 A | 11/1999 | Veltri et al. | |
| 6,037,458 A | 3/2000 | Hirai et al. | |
| 6,054,121 A | 4/2000 | Cerami et al. | |
| 6,071,517 A | 6/2000 | Fanger et al. | |
| 6,126,918 A | 10/2000 | Pepys et al. | |
| 6,174,526 B1 | 1/2001 | Cerami et al. | |
| 6,365,570 B1 * | 4/2002 | Van Kessel et al. | 514/1.4 |
| 6,406,698 B1 * | 6/2002 | Svehang et al. | 424/184.1 |
| 6,537,811 B1 | 3/2003 | Freier | |
| 6,600,019 B2 | 7/2003 | Prayaga et al. | |
| 6,660,843 B1 | 12/2003 | Feige et al. | |
| 6,872,541 B2 | 3/2005 | Mills | |
| 7,666,432 B2 * | 2/2010 | Gomer et al. | 424/198.1 |
| 7,763,256 B2 | 7/2010 | Gomer et al. | |
| 8,012,472 B2 | 9/2011 | Gomer et al. | |
| 8,057,802 B2 | 11/2011 | Gomer et al. | |
| 8,187,599 B2 | 5/2012 | Gomer et al. | |
| 8,187,608 B2 | 5/2012 | Gomer et al. | |
| 8,247,370 B2 | 8/2012 | Pelura | |
| 8,329,659 B2 | 12/2012 | Willett | |
| 8,497,243 B2 * | 7/2013 | Hesson et al. | 514/13.2 |
| 2002/0058284 A1 | 5/2002 | Winkel | |
| 2003/0003567 A1 | 1/2003 | Barber et al. | |
| 2003/0022245 A1 | 1/2003 | Mills | |
| 2003/0162180 A1 | 8/2003 | Pricop | |
| 2004/0068095 A1 | 4/2004 | Shimkets et al. | |
| 2004/0121343 A1 | 6/2004 | Buechler et al. | |
| 2005/0182042 A1 | 8/2005 | Feldman et al. | |
| 2005/0238620 A1 | 10/2005 | Gomer et al. | |
| 2007/0048855 A1 | 3/2007 | Gamez et al. | |
| 2007/0065368 A1 | 3/2007 | Gomer et al. | |
| 2009/0074754 A1 | 3/2009 | Hesson et al. | |
| 2009/0202520 A1 | 8/2009 | Lupher, Jr. et al. | |
| 2010/0111898 A1 | 5/2010 | Pelura | |
| 2010/0260781 A1 | 10/2010 | Murray | |
| 2010/0266578 A1 * | 10/2010 | Murray | 424/130.1 |
| 2010/0317596 A1 * | 12/2010 | Willett et al. | 514/20.9 |
| 2010/0323970 A1 | 12/2010 | Willett | |

FOREIGN PATENT DOCUMENTS

| | | |
|---|---|---|
| EP | 0 206 302 A2 | 12/1986 |
| EP | 1 090 630 A1 | 4/2001 |
| JP | 11-319542 | 11/1999 |
| WO | WO 92/21364 A1 | 12/1992 |
| WO | WO 94/27640 A1 | 12/1994 |
| WO | WO 95/05394 A1 | 2/1995 |
| WO | WO 95/33454 A1 | 12/1995 |
| WO | WO 97/16568 | 5/1997 |
| WO | WO 97/26906 A1 | 7/1997 |
| WO | WO 99/41285 A1 | 8/1999 |
| WO | WO 99/45900 A1 | 9/1999 |
| WO | WO 01/74300 A1 | 10/2001 |

(Continued)

OTHER PUBLICATIONS http://en.wikipedia.org/wiki/Pentraxins.*
http://en.wikipedia.org/wiki/Serum_amyloid_P_component.*
Boysen et al., "Recombinant human serum amyloid P component from *Pichia pastoris:* production and characterization," Protein Expression & Purification, vol. 35(2), pp. 284-292, XP004506564 (2004).
Heegaard, Niels H.H., "Microscale characterization of the structure-activity relationship of a heparin-binding glycopeptide using affinity capillary electrophoresis and immobilized enzymes," Journal of Chromatography, vol. 853(1-2), pp. 189-195, XP004178238 (1999).

(Continued)

*Primary Examiner* — Maury Audet
(74) *Attorney, Agent, or Firm* — Ropes & Gray LLP; Melissa S. Rones; Brian M. Gummow

(57) ABSTRACT

One aspect of the present invention relates to the surprising discovery that modification of a glycan structure on a human SAP polypeptide can increase the biological activity of the SAP polypeptide relative to a corresponding sample of wild-type SAP isolated from human serum. The disclosure provides both variant human SAP polypeptides and methods for making the same. In particular, the present invention provides methods and compositions for in vitro and in vivo addition, deletion, or modification of sugar residues to produce SAP polypeptides, such as a human SAP polypeptide, having a desired glycosylation pattern.

52 Claims, 10 Drawing Sheets

(56) References Cited

FOREIGN PATENT DOCUMENTS

Figure 1:
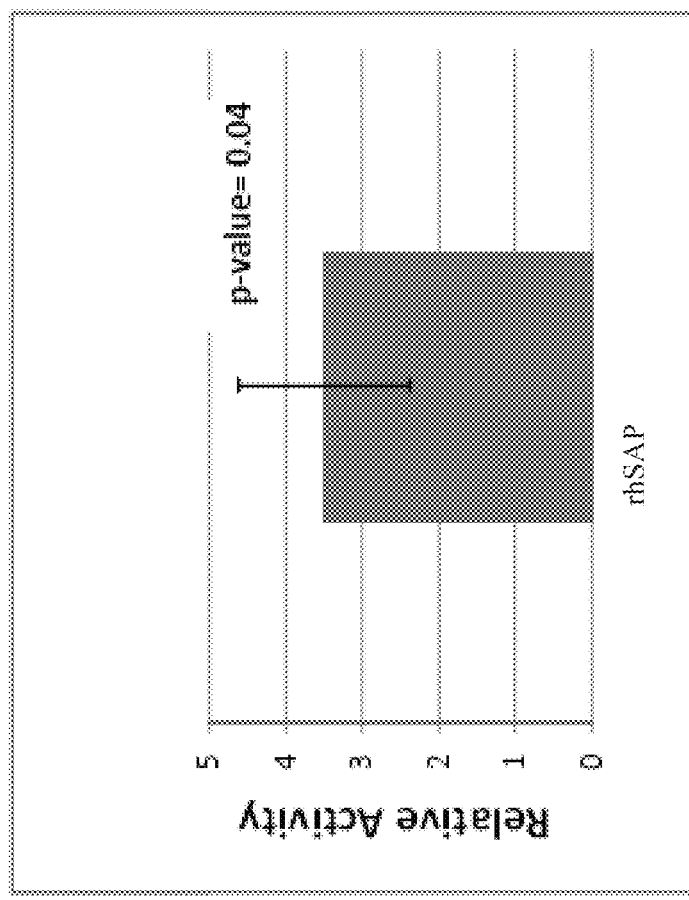
Figure 2A:
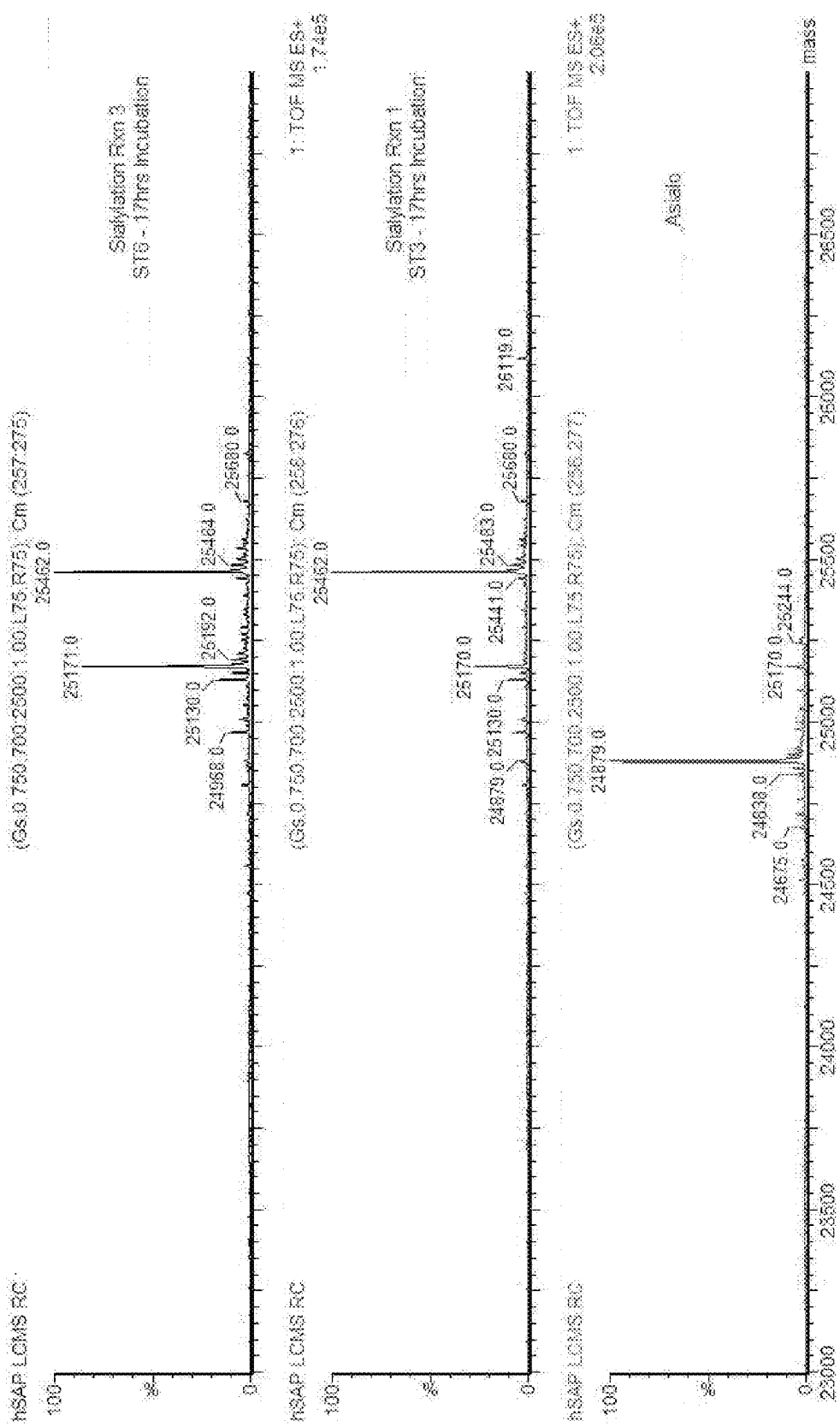
Figure 2B:
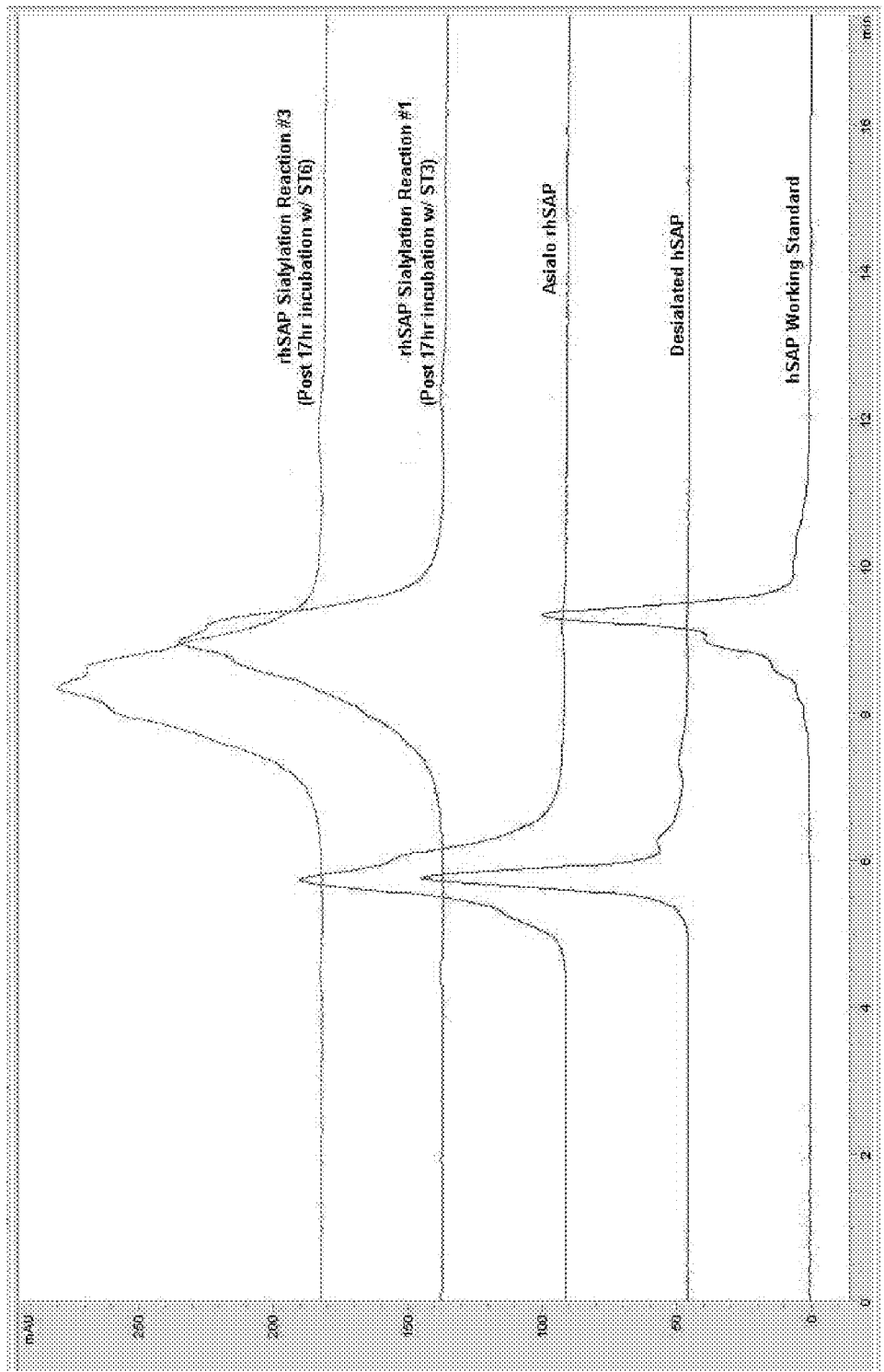
Figure 2C:
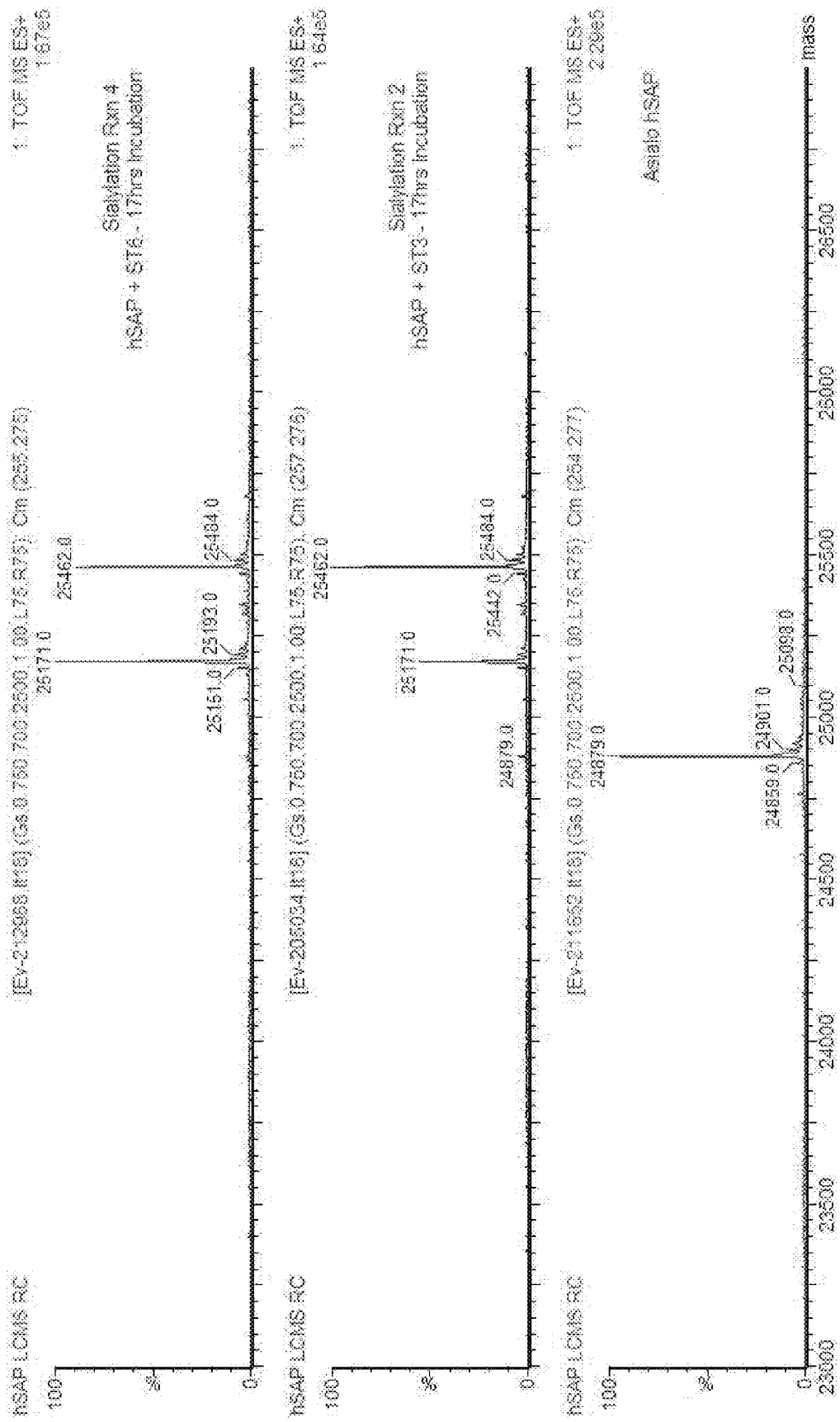
Figure 2D:
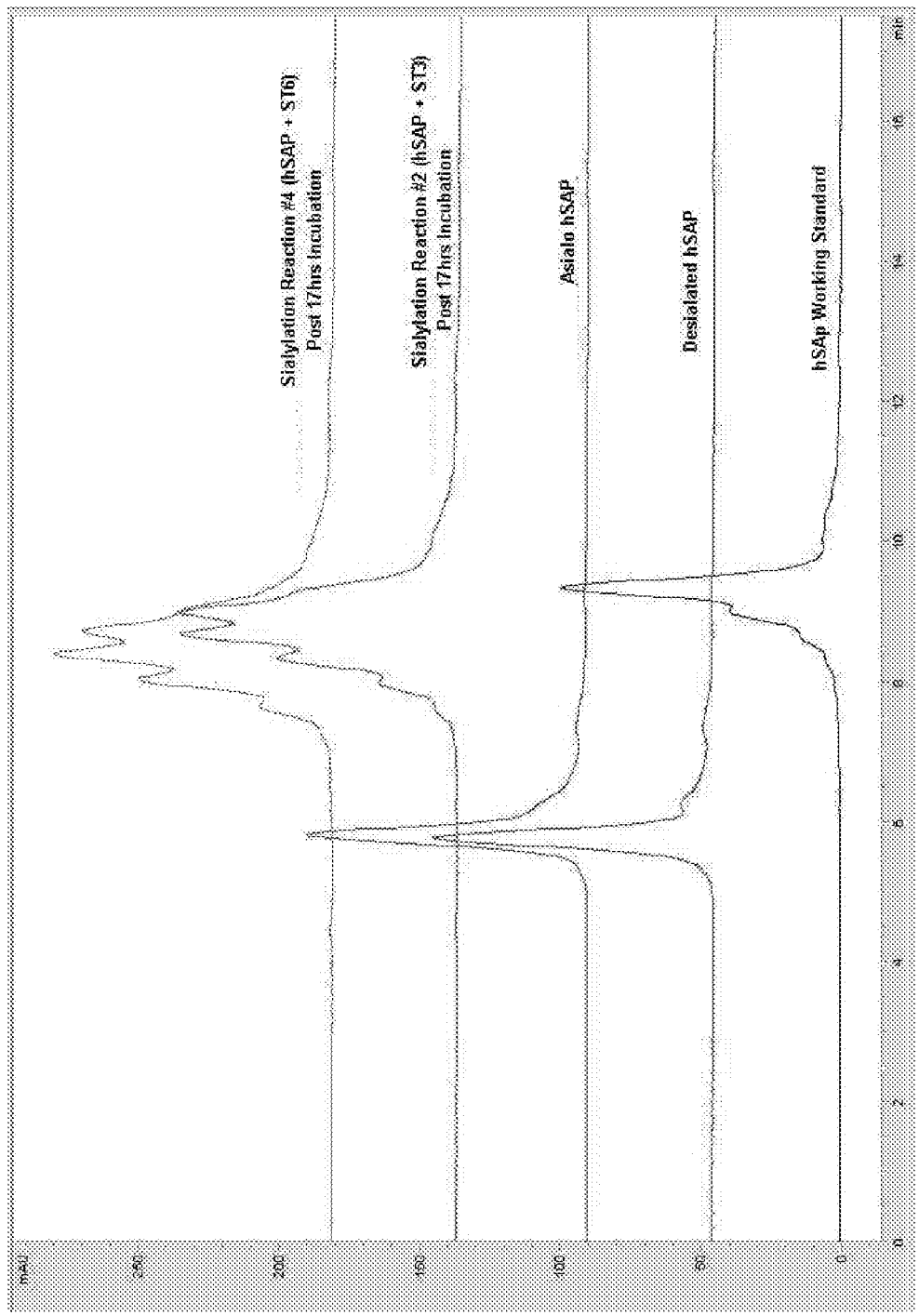
Figure 2E:
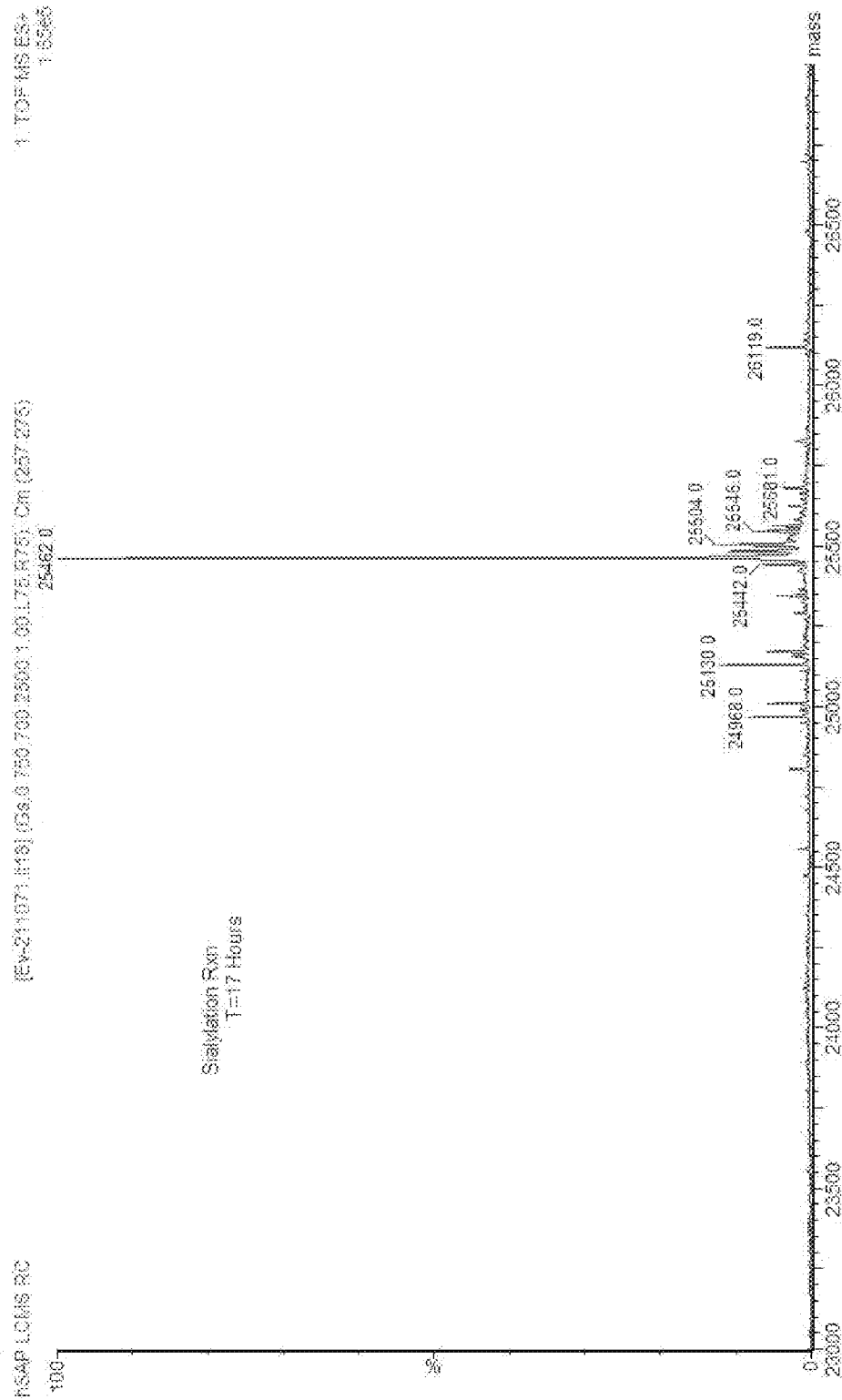
Figure 2F:
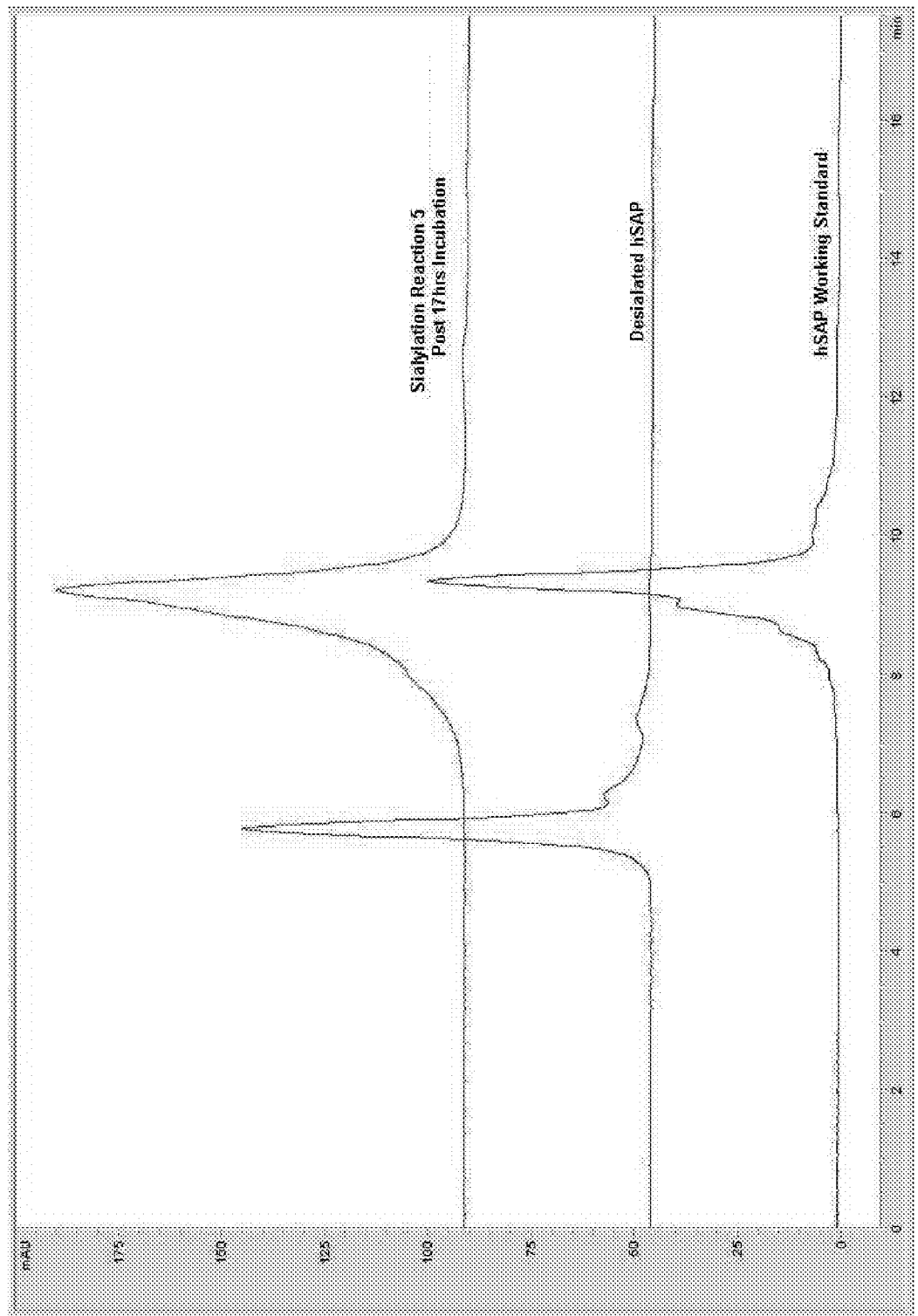

| WO | WO 03/031572 A2 | 4/2003 |
|---|---|---|
| WO | WO 03/097104 A1 | 11/2003 |
| WO | WO 2004/009823 A1 | 1/2004 |
| WO | WO 2004/016750 A2 | 2/2004 |
| WO | WO 2004/058292 A2 | 7/2004 |
| WO | WO 2004/059293 A2 | 7/2004 |
| WO | WO 2004/059318 A2 | 7/2004 |
| WO | WO 2004/076486 A1 | 9/2004 |
| WO | WO 2005/110474 A2 | 11/2005 |
| WO | WO 2005/115452 A2 | 12/2005 |
| WO | WO 2006/002438 A2 | 1/2006 |
| WO | WO 2006/002930 A2 | 1/2006 |
| WO | WO 2006/028956 A2 | 3/2006 |
| WO | WO 2006/039418 A2 | 4/2006 |
| WO | WO 2007/047207 A2 | 4/2007 |
| WO | WO 2007/047796 A2 | 4/2007 |
| WO | WO 2008/070117 A1 | 6/2008 |
| WO | WO 2009/009019 A2 | 1/2009 |
| WO | WO 2009/009034 A2 | 1/2009 |
| WO | WO 2010/104959 A1 | 9/2010 |
| WO | WO 2010/104961 A1 | 9/2010 |
| WO | WO 2010/115032 A1 | 10/2010 |
| WO | WO 2010/141918 A1 | 12/2010 |

OTHER PUBLICATIONS

Hamazaki, Hideaki, "Structure and significance of N-linked sugar unit of human serum amyloid P component," *Biochimica et Biochimica Acta*, 1037(3):435-438 (1990).

Kiernan et al., "Proteomic characterization of novel serum amyloid P component variants from human plasm and urine," *Proteomics*, 4:1825-1829 (2004).

Siebert et al., "Comparison between intact and desialylated human serum amyloid P component by laser photo CIDNP (checmically induced dynamic nuclear polarization) technique: an indication for a conformational impact of sialic acid," Glycoconjugate Journal, vol. 14(8), pp. 945-949, XP55040970 (1997).

Siebert et al., "Effect of enzymatic desialylation of human serum amyloid P component on surface exposure of laser photo CIDNP (chemically induced dynamic nuclear polarization)—reactive histidine, tryptophan and tyrosine residues," *FEBS Letters*, 371(1):13-6 (1995).

Hamazaki, Hideaki, "Structure and significance of N-linked sugar unit of human serum amyloid P component," *Bichimica et Biophysica Acta*, 1037(3):435-438 (1990).

Kieran et al., "Proteomic characterization of novel serum amyloid P component variants from human plasm and urine," *Proteomics*, 4:1825-1829 (2004).

Murray et al., "Serum amyloid P therapeutically attenuates murine bleomycin-induced pulmonary fibrosis via its effects on macrophages," *PLoS One*, 5(3):e968 pp. 1-9 (2010).

Pepys et al., Glycobiology of Human Serum Amyloid P Component Amyloid Amyloidosis, *Proc. Int. Symp. Amyloidosis*, pp. 177-179 (1994).

Pepys et al., "Human serum amyloid P component is an invariant constituent of amyloid deposits and has a uniquely homogeneous glycostructure," *PNAS*, 91:5206-5606 (1994).

International Search Report, PCTUS/2010/037542 dated Sep. 9, 2010.

Abe, R., et al., "Peripheral Blood Fibrocytes: Differentiation Pathway and Migration to Wound Sites," The Journal of Immunology, 166(12):7556-7562 (2001).

Agostini, et al., "Chemokine/Cytokine Cocktail in Idiopathic Pulmonary Fibrosis," Proc. Am. Thorac. Soc., 3(4):357-363 (2006).

Aiba, S., et al., "Immunoglobulin-Producing Cells in Plasma Cell Orificial Mucositis," Journal of Cutaneous Pathology, 16(4):207-210 (1989).

Alles, V. V., et al., "Inducible expression of PTX3, a new member of the pentraxin family, in human mononuclear phagocytes," Blood, 84(10):3483-3493 (1994).

Ashcroft, T., et al., "Simple Method of Estimating Severity of Pulmonary Fibrosis on a Numerical Scale," J Clin Pathol, 41(4):467-470 (1988).

Ashikawa, K., et al., "Piceatannol Inhibits TNF-Induced NF-κB Activation and NF-κB-Mediated Gene Expression Through Suppression of IκBα Kinase and p65 Phosphorylation," The Journal of Immunology, 169(11):6490-6497 (2002).

Azuma, H., et al., "Superagonistic CD28 Antibody Induces Donor-Specific Tolerance in Rat Renal Allografts," American Journal of Transplantation, 8(10):2004-2014 (2008).

Bain, J., et al., "The Specificities of Protein Kinase Inhibitors: An Update," Biochem. J, 371(Pt 1):199-204 (2003).

Barna, B. P., et al., "Activation of Human Monocyte Tumoricidal Activity by C-Reactive Protein," Cancer Research, 47(5):3959-3963 (1987).

Bharadwaj et al., "Serum amyloid P component binds to Fc gamma receptors and opsonizes particles for phagocytosis," *The Journal of Immunology*, 166:6735-6741 (2001).

Bharadwaj, D., et al., "The Major Receptor for C-Reactive Protein on Leukocytes Is Fcγ Receptor II," The Journal of Experimental Medicine, 190(4):585-590 (1999).

Bickerstaff, M. C. M., et al., "Serum Amyloid P Component Controls Chromatin Degradation and Prevents Antinuclear Autoimmunity," Nature Medicine, 5(6):694-697 (1999).

Biro, E., et al., "Activated Complement Components and Complement Activator Molecules on the Surface of Cell-Derived Microparticles in Patients with Rheumatoid Arthritis and Healthy Individuals," Annals of the Rheumatic Diseases, 66(8):1085-1092 (2007).

Bodman-Smith, K. B., et al., "C-Reactive Protein-Mediated Phagocytosis and Phospholipase D Signalling Through the High-Affinity Receptor for Immunoglobulin G (FcγRI)," The Journal of Immunology, 107(2):252-260 (2002).

Booth, D. R., et al., Analysis of autoaggregation and ligand binding sites of serum amyloid P component by in vitro mutagenesis. From Amyloid & Amyloidosis 1998: Proceedings of the VIIIth International Symposium on Amyloidosis, Rochester, MN, pp. 23-25 (Aug. 7-11, 1998).

Brown, E. J., "The Role of Extracellular Matrix Proteins in the Control of Phagocytosis," Journal of Leukocyte Biology, 39(5):579-591 (1986).

Brown, M. R., et al., "Receptor-Ligand Interactions Between Serum Amyloid P Component and Model Soluble Immune Complexes," The Journal of Immunology, 151(4):2087-2095 (1993).

Bucala, R., et al., "Circulating Fibrocytes Define a New Leukocyte Subpopulation That Mediates Tissue Repair," Molecular Medicine, 1(1):71-81 (1994).

Cappiello, M. G., et al., "Suppression of IL-12 Transcription in Macrophages Following Fcγ Receptor Ligation," The Journal of Immunology, 166(7):4498-4506 (2001).

Castaño, A. P., et al., "Serum Amyloid P Inhibits Fibrosis Through FcγR-Dependent Monocyte-Macrophage Regulation in Vivo," Sci. Transl. Med. 1(5):1-26 (2009).

Chatziantoniou, et al., "Is Kidney Injury a Reversible Process," Curr. Opin. Nephrol. Hypertension, 17(1):76-81 (2008).

Chen, J., et al., "Platelet FcγRIIA His131Arg Polymorphism and Platelet Function: Antibodies to Platelet-Bound Fibrinogen Induce Platelet Activation," Journal of Thrombosis and Haemostasis, 1(2):355-362 (2003).

Chesney, J., et al., "Peripheral Blood Fibrocytes: Mesenchymal Precursor Cells and the Pathogenesis of Fibrosis," Curr. Rheumatology Reports, 2(6):501-505 (2000).

Chesney, J., et al., "Regulated Production of Type I Collagen and Inflammatory Cytokines by Peripheral Blood Fibrocytes," The Journal of Immunology, 160(1):419-425 (1998).

Chesney, J., et al., "The Peripheral Blood Fibrocyte is a Potent Antigen-Presenting Cell Capable of Priming Naive T Cells in Situ," Journal of Immunology, 94(12):6307-6312 (1997).

Chi, M., et al., "C-Reactive Protein Induces Signaling Through FcγRIIa on HL-60 Granulocytes," The Journal of Immunology, 168:1413-1418 (2002).

(56) References Cited

OTHER PUBLICATIONS

Christner, R. B., et al., "Binding of Human Serum Amyloid P-Component to Phosphocholine", Archives of Biochemistry and Biophysics, 314(2):337-343 (1994).
Clark, R. A. F., "Fibrin and Wound Healing," Annals New York Academy of Sciences 936:355-367 (2001).
Crouch, E., "Pathobiology of Pulmonary Fibrosis," Am J Physiol Lung Cell Mol Physiol, 259(4 Pt 1):L159-L184 (1990).
D'Andrea, A., et al., "Stimulatory and Inhibitory Effects of Interleukin (IL)-4 and IL-13 on the Production of Cytokines by Human Peripheral Blood Mononuclear Cells: Priming for IL-12 and Tumor Necrosis Factor α Production," J Exp Med, 181(2):537-546 (1995).
Daëron, M., "Fc Receptor Biology," Annual Review of Immunology 15:203-234 (1997).
Daëron, M., "Structural Bases of FcγR Functions," Int Rev Immunol. 16(1-2):1-27 (1997).
De Beer, F. C., et al., "Fibronectin and C4-Binding Protein are Selectively Bound by Aggregated Amyloid Component", J Exp Med., 154(4):1134-1149 (1981).
De Beer, F. C., et al., "Isolation and Characterization of C-Reactive Protein and Serum Amyloid P Component in the Rat," Immunology 45(1):55-70 (1982).
De Beer, F. C., et al., "Isolation of Human C-Reactive Protein and serum Amyloid P Component," Journal of Immunological Methods, 50(1):17-31 (1982).
de Haas, C. J. C., et al., "A Synthetic Lipopolysaccharide-Binding Peptide Based on Amino Acids 27-39 of Serum Amyloid P Component Inhibits Lipopolysaccharide-Induced Responses in Human Blood," The Journal of Immunology, 161(7):3607-3615 (1998).
De Paepe, et al., "Hydrogels Based on Agarose and Agarose/Gelatin Blends", International Journal of Artificial Organs, vol. 24, No. 8, p. 543, XP009108972 and XXVIII Congress of the European Society for Artificial Organs on Bridging the Interdisciplinarity; Gent, Belgium; Sep. 22-25, 2001.
Du Clos, T. W., "C-Reactive Protein Reacts With the U1 Small Nuclear Ribonucleoprotein," The Journal of Immunology, 143(8):2553-2559 (1989).
Du Clos, T. W., et al., "Reply to Human C-reactive protein does not bind to FcγRIIa on phagocytic cells," The Journal of Clinical Investigation, vol. 107(5):643 (2001).
Duchemin, A. M., et al., "Association of Non-Receptor Protein Tyrosine Kinases with the FcγRI/γ-Chain Complex in Monocytic Cells," The Journal of Immunology, 158(2):865-871 (1997).
Duckworth, et al., "The Structure of Agar Part I. Fractionation of a Complex Mixture of Polysaccharides," Carbohydrate Research, 16:189-197 (1971).
Emsley, J., et al., "Structure of Pentameric Human Serum Amyloid P Component," Nature 367(6461):338-345 (1994).
Flesch, B. K., et al., "The FCGR2A—Arg131 Variant is no Major Mortality Factor in the Elderly—Evidence From a German Centenarian Study," International Journal of Immunogenetics, 33(4):277-279 (2006).
Garden, A. S., et al., "Head and Neck Radiation and Mucositis," 1(1):30-34 (2007).
Gehring, et al., "Effect of Topically Applied Dexpanthenol on Epidermal Barrier Function and Stratum Corneum Hydration," Arzneim-Forsch./Drug Res., 50(11):7 (2000).
Gerhard, et al., "The Status, Quality and Expansion of the NIH Full-Length cDNA Project: The Mammalian Gene Collection (MGC)," Genome Research, 14(10B):2121-2127 (2004).
Gewurz, H., et al., "Structure and Function of the Pentraxins," Current Opinion in Immunology, 7(1):54-64 (1995).
Ghazizadeh, S., et al., "Physical and Functional Association of Src-Related Protein Tyrosine Kinases with FcγRII in Monocytic THP-1 Cells," Journal of Biological Chemistry, 269(12):8878-8884 (1994).
Giorgini, A., et al., "Blockade of Chronic Graft-Versus-Host Disease by Alloantigen-induced CD4+CD25+Foxp3+ Regulatory T Cells in Nonlymphopenic Hosts," Journal of Leukocyte Biology, 82(5):1053-1061 (2007).

Giri, S., et al., "Antifibrotic Effect of Decorin in a Bleomycin Hamster Model of Lung Fibrosis," Biochemical Pharmacology, 54:1205-1216 (1997).
Gregory, S. G., et al., "The DNA Sequence and Biological Annotation of Human Chromosome 1", Nature 441(7091):315-321 (2006).
Guyre, C. A., et al., "Receptor Modulation by FcγRI-Specific Fusion Proteins is Dependent on Receptor Number and Modified by IgG," The Journal of Immunology, 167(11):6303-6311 (2001).
Harris, J. M., et al., "Pegylation a Novel Process for Modifying Pharmacokinetics," Clin. Pharmacokinetics, 40(7):539-551 (2001).
Hartlapp, I., et al., "Fibrocytes Induce an Angiogenic Phenotype in Cultured Endothelial Cells and Promote Angiogenesis in Vivo," The FASEB Journal, 15(12):2215-2224 (2001).
Heegaard, N. H. H., et al., "Ligand-Binding Sites in Human Serum Amyloid P Component," Eur. J. Biochem. 239(3):850-856 (1996).
Hicks et al., "Serum amyloid P component binds to histones and activates the classical complement pathway", The Journal of Immunology, 149:3689-3694 (1992).
Hind, C. R. K., et al., "Human Serum Amyloid P Component, a Circulating Lectin with Specificity for the Cyclic 4,6-Pyruvate Acetal of Galactose: Interactions with Various Bacteria", Biochem.J., 225(1):107-111 (1985).
Hind, C. R., et al, "Binding specificity of serum amyloid P-component for the pyruvate acetal of galactose," Journal of Experimental Medicine, 159(4):1058-1069 (1984).
Hohenester, E., et al., "Crystal Structure of a Decameric Complex of Human Serum Amyloid P Component with Bound dAMP", J. Mol. Biol. 269(4):570-578 (1997).
Huang, Z. Y., et al., "The Monocyte Fγy Receptors FcγRI/γ and FcγRIIA Differ in their Interaction with Syk and with Src-Related Tyrosine Kinases," J Leukoc Biol 76(2):491-499 (2004).
Hundt, M., et al., "Treatment of Acute Exacerbation of Systemic Lupus Erythematosus with High-Dose Intravenous Immunoglobulin," Rheumatology (Oxford), 39(11):1301-1302 (2000).
Hutchinson, W. L. , et al., "Human Serum Amyloid P Component is a Single Uncomplexed Pentamer in Whole Serum," Molecular Medicine, 6(6):482-493 (2000).
Ishaque, et al., "Role of Vitamins in Determining Apoptosis and Extent of Suppression by bel-2 During hybridoma Cell Culture," Apoptosis, 7(3):231-239 (2002).
Janeway, et al., Immunobiology, 3rd edition, Garland Publishing, pp. 3:1-3:11 (1997).
Jenny, N.S., et al., "Serum Amyloid P and Cardiovascular Disease in Older Men and Women Results from the Cardiovascular Health Study," Arterioscler. Thromb. Vasc. Biol., 27:352-358 (2007).
Junqueira, L. C.,et al., "Picrosirius Straining Plus Polarization Microscopy, a Specific Method for Collagen Detection in Tissue Sections," Histochem. J, 11(4):447-455 (1979).
Kessel, A., et al., Intravenous Immunoglobulin Therapy Affects T Regulatory Cells by Increasing Their Suppressive Function, The Journal of Immunology, 179(8):5571-5575 (2007).
Kiernan, U.A., et al., "Selected Expression Profiling of Full-Length Proteins and Their Variants from Human Plasma," Clin. Proteomics 1:7-16 (2004).
Kinoshita CM, et al., "A Protease-Sensitive Site in the Proposed Ca2+-Binding Region of Human Serum Amyloid Component and Other Pentraxins." Protein Sci., 1:700-709 (1992).
Kisseleva, T., et al., "Bone Marrow-Derived Fibrocytes Participate in Pathogenesis of Liver Fibrosis," Journal of Hepatology, 45(3):429-438 (2006).
Kivela-Rajamaki, M. J., et al., "Laminin-5-γ2-chain and collagenase-2 (MMP-8) in Human Peri-Implant Sulcular Fluid," Clin. Oral Implants Res., 14(2):158-165 (2003).
Kolstoe et al., "Molecular dissection of Alzheimer's disease neuropathology by depletion of serum amyloid P component", *PNAS*, 106(18):7619-7623 (2009).
Korade-Mirnics, Z.,et al., "Src Kinase-Mediated Signaling in Leukocytes," J Leukoc Biol., 68(5):603-613 (2000).
Kucuk, H. F., et al., "Effect of a Selective Cyclooxygenase-2 Inhibitor on Renal Scarring," European Surgical Research, 38(5):451-457 (2006).

(56) References Cited

OTHER PUBLICATIONS

Lai, J. Y., et al., "Potent Small Molecule Inhibitors of Spleen Tyrosine Kinase (Syk)," Bioorganic & Medicinal Chemistry Letters, 13(18):3111-3114 (2003).
Lei, K. K., et al., "Genomic DNA Sequence for Human C-Reactive Protein," J. Biol. Chem. 260(24):13377-13383 (1985).
Lindenbaum, E. S., et al., "Serum-Free Cell Culture Medium Induces Acceleration of Wound Healing in Guinea-Pigs," Burns, 21(2):110-115 (1995).
Liu, T., et al., "Human Plasma N-Glycoproteome Analysis by Immunoaffinity Subtraction, Hydrazide Chemistry and Mass Spectrometry," J. Proteome Res., 4(6):2070-2080 (2005).
Lu, J., et al., "Structural Recognition and Functional Activation of FcγR by Innate Pentraxins," Nature, 456(7224):989-992 (2008).
Majno, G., "Chronic Inflammation: Links With Angiogenesis and Wound Healing," American Journal of Pathology, 153(4):1035-1039 (1998).
Mantzouranis, E. C., et al., "Human Serum Amyloid P Component, cDNA Isolation, Complete Sequence of Pre-Serum Amyloid P Component, and Localization of the Gene to Chromosome 1," The Journal of Biological Chemistry, 260(12):7752-7756 (1985).
Marnell, L. L., et al., "C- Reactive Protein Binds to FcγRI in Transfected COS Cells," The Journal of Immunology, 155(4):2185-193 (1995).
Metz, C. N., "Fibrocytes: A Unique Cell Population Implicated in Wound Healing," Cell. Mol. Life Sci., 60(7):1342-1350 (2003).
Mold, C., et al., "Serum Amyloid P Component and C-Reactive Protein Mediate Phagocytosis Through Murine FcγRs," The Journal of Immunology, 166(2):1200-1205 (2001).
Moore, B. B., et al., "CCR2-Mediated Recruitment of Fibrocytes to the Alveolar Space After Fibrotic Injury," American Journal of Pathology, 166(3):675-684 (2005).
Mori, L., et al., "Fibrocytes Contribute to the Myofibroblast Population in Wounded Skin and Originate From the Bone Marrow," Exp Cell Res., 304(1):81-90 (2005).
Mortensen, R. F., et al., "Regulation of phagocytic leukocyte activities by C-reactive protein," Journal of Leukocyte Biology, 67(4):495-500 (2000).
Murphy, T. M., et al., "Extrahepatic Transcription of Human C-Reactive Protein," Journal of Experimental Medicine, 73(2):495-498 (1991).
Ohnishi, S. et al., "Isolation and Characterization of the Complete Complementary and Genomic DNA Sequences of Human Serum Amyloid P Component," J. Biochem, 100(4):849-858 (1986).
Oliveira, E. B., et al., "Primary Structure of Human C-Reactive Protein," The Journal of Biological Chemistry, 254(2):489-502 (1979).
Oriente, A., et al., "Interleukin-13 Modulates Collagen Homeostasis in Human Skin and Keloid Fibroblasts," The Journal of Pharmacology and Experimental Therapeutics, 292(3):988-994 (2000).
Osmand, A. P., et al., Partial Amino-Acid Sequences of Human and Rabbit C-Reactive Proteins: Homology with Immunoglobulins and Histocompatibility Antigens, Proc. Natl. Acad. Sci. U.S.A., 74(3):1214-1218 (1977).
Pachence, J., et al., "Tissue-Activated Delivery—Novel Methods for Site-Directed Drug Delivery," Drug Delivery Technology, 3(1):40-45 (2003).
Painter, R. H., "Evidence that C1t (Amyloid P-component) is not a subcomponent of the first component of complement (C1)," J. Immunol., 119(6):2203-2205 (1977).
Paul, William E., M.D., editor, Fundamental Immunology, 3d ed. Raven Press, p. 242 (1993).
Pepys, et al., "Targeted pharmacological depletion of serum amyloid P component for treatment of human amyloidosis", Nature, 471:254-259 (2002).
Pepys, M. B., "Isolation of serum amyloid P-component (Protein SAP) in the Mouse," Immunology, 37(3):637-641 (1979).
Pepys, M. B., et al., "Amyloid P Component. A Critical Review," Amyloid: Int. J. Exp. Invest., 4(4):274-295 (1997).
Pepys, M. B., et al., "Serum Amyloid P Component is the Major Calcium-Dependent Specific DNA Binding Protein of Serum," Biochemical and Biophysical Research Communications, 148(1):308-313 (1987).
Pepys, MB, Serum Amyloid P. Component. Structure, Function and Role in Amlyoidosis. From Amlyoid & Amyloidosis 1998: Proceedings of the VIIIth International Symposium on Amyloidosis, Rochester, MN, pp. 6-10 (Aug. 7-11, 1998).
Philips, R. J., et al., "Circulating Fibrocytes Traffic to the Lungs in Response to CXCL 12 and Mediate Fibrosis," The Journal of Clinical Investigation, 114(3):438-446 (2004).
Pilling et al., "Aggregated IgG inhibits the differentiation of human fibrocytes," Journal of Leukocyte Biology, 79:1242-1251 (2006).
Pilling, D. et al., "Inhibition of Fibrocyte Differentiation by Serum Amyloid P.," The Journal of Immunology, 17(10):5537-5546 (2003).
Pilling, D., et al., "Reduction of Bleomycin-Induced Pulmonary Fibrosis by Serum Amyloid P," The Journal of Immunology, 179(6):4035-4044 (2007).
Pontet, M., et al., "One step preparation of both human C-reactive protein and Cit," FEBS Letters, 88(2):172-175 (1978).
Portolano et al., "Lack of Promiscuity in Autoantigen-Specific H and L Chain Combinations as Revealed by Human H and L Chain "Roulette"," J. Immunol., 150(3):880-887 (1993).
Potempa, L. A., et al., "Effect of Divalent Metal Ions and pH Upon the Binding Reactivity of Human Serum Amyloid P Component, a C-Reactive Protein Homologue, for Zymosan," The Journal of Biological Chemistry, 260(22):12142-12147 (1985).
Prelli, F., et al., "The Primary Structure of Human Tissue Amyloid P Component From a Patient with Primary Idiopathic Amyloidosis," The Journal of Biological Chemistry, 260(24):12895-12898 (1985).
Quan et al., "The role of circulating fibrocytes in fibrosis" Current Rheumatology Reports. 8(2):145-150 (2006).
Rudikoff et al., "Single amino acid substitution altering antigen-binding specificity," Proc Natl Acad Sci USA, 79(6):1979-1983 (1982).
Russo, F. P., et al., "The Bone Marrow Functionally Contributes to Liver Fibrosis," Gastroenterology, 130(6):1807-1821 (2006).
Russo, et al., "Liver Fibrosis; Bone Marrow Functionally Contributes to Liver Fibrosis," 130(6) Gastroenterology Week Jul. 31, 2006 pp. 83-84 (2006).
Sada, K., et al., "Structure and Function of Syk Protein-Tyrosine Kinase," J Biochem, 130(2):177-186 (2001).
Saeland, E., at al., "Human C-reactive Protein Does not Bind to FcγRIIa on Phagocytic Cells," The Journal of Clinical Investigation, 107(5):641-643 (2001).
Sawada et al., "The Ace Inhibitor, Quinapril, Ameliorates Peritoneal Fibrosis in an Encapsulating Peritoneal Sclerosis Model in Mice" Pharmacological Research. 46(6): 505-510 (2002).
Schmidt, M., et al., "Identification of Circulating Fibrocytes as Precursors of Bronchial Myofibroblasts in Asthma," The Journal of Immunology, 171(1):380-389 (2003).
Schwalbe, et al., "Pentraxin Family of Proteins Interact Specifically with Phosphorylcholine and/or Phosporylethanolamine," Biochemistry, 31:4907-1645 (1992).
Shoenfeld, Y., et al., "The mosaic of Autoimmunity: Prediction, Autoantibodies, and Therapy in Autoimmune Diseases—2008," Israel Medical Association Journal, 10(1):13-19 (2008).
Shrive, A. K., et al., "Three Dimensional Structure of Human C-Reactive Protein," Nature Structural Biology, 3(4):346-354 (1996).
Sjoblom, T., et al., "The Consensus Coding Sequences of Human Breast and Colorectal Cancers," Science, 314(5797):268-274 (2006).
Srinivasan, N., et al., "Comparative Analyses of Pentraxins: Implications for Protomer Assembly and Ligand Binding," Structure, 2(11):1017-1027 (1994).
Steel, D. M., et al., "The Major Acute Phase Reactants: C-Reactive Protein, Serum Amyloid P Component and Serum Amyloid A Protein," Immunology Today, 15(2):81-88 (1994).
Stein, M. P., et al., "C-reactive Protein Binding to FcγRIIa on Human Monocytes and Neutrophils is Allele-Specific," The Journal of Clinical Investigation, 105(3):369-376 (2000).

(56) References Cited

OTHER PUBLICATIONS

Su, L., et al., "Distinct Mechanisms of STAT Phosphorylation Via the Interferon-Alpha/Beta Receptor, Selective Inhibition of STAT3 and STAT5 by Piceatannol," Journal of Biological Chemistry 275(17):12661-12666 (2000).
Sutterwala, F. S., et al., "The Taming of IL-12 Suppressing the production of Proinflammatory Cytokines," Journal of Leukocyte Biology, 65(5):543-551 (1999).
Thompson, A. R., et al., "Human Plasma P Component: Isolation and Characterization," Biochemistry, 17(20):4304-4311 (1978).
Thompson, D., et al., "The Physiological Structure of Human C-Reactive Protein and its Complex with Phosphocholine", Structure, 7(2):169-177 (1999).
Thomson, C. W., et al., "Lentivirally Transduced Recipient-Derived Cells to Ex Vivo Expand Functional FcRγ-Sufficient Double-Negative Regulatory T cells," Molecular Therapy, 15(4):818-824 (2007).
Toubi, E., et al., "High Dose Intravenous Immunoglobulins: An Option in the Treatment of Systemic Lupus Erythematosus," Human Immunology, 66(4):395-402 (2005).
Tridandapani, S., et al., "Regulated Expression and Inhibitory Function of Fcγ-RIIb in Human Monocytic Cells," Journal of Biological Chemistry, The American Society for Biochemistry and Molecular Biology, Inc, 277(7):5082-5089 (2002).
Trinchieri, G., "Interleukin-12 and the Regulation of Innate Resistance and Adaptive Immunity," Nature Reviews Immunology, 3(2):133-146 (2003).
Tucci, A., et al., "Biosynthesis and Postsynthetic Processing of Human C-Reactive Protein," The Journal of Immunology, 131(5):2416-2419 (1983).
Turner, M., et al., "Tyrosine Kinase SYK: Essential Functions for Immunoreceptor Signalling," Immunology Today, 21(3):148-154 (2000).
Underwood, D. C., et al., "SB 239063, a p38 MAPK Inhibitor, reduces Neutrophilia, Inflammatory Cytokines, MMP-9, and Fibrosis in Lung," Am J Physiol Lung Cell Mol Physiol, 279:L895-L902 (2000).
Volanakis, J.E., "Human C-Reactive Protein: Expression, Structure, and Function," Molecular Immunology, 38(2-3):189-197 (2001).
Wang, Q., et al., "Effect of Antibody Against Integrin α4 on Bleomycin-Induced Pulmonary Fibrosis in Mice," Biochemical Pharmacology, 60:1949-1658 (2000).
Weimann, et al., "Studies of Wound Healing: Effects of Calcium D-Panthothenate on the Migration, Proliferation and Protein Synthesis of Human Dermal Fibroblasts in Culture," Interat. J. Vit. Nutr. Res., 69(2):113-119 (1999).
Whitehead, A. S., et al., "Isolation of Human C-Reactive Protein Complementary DNA and Localization of the Gene to Chromosome 1," Science, 221(4605):69-71 (1983).
Woo, P., et al., "Characterization of Genomic and Complementary DNA Sequence of Human C-Reactive Protein, and Comparison with the Complemen ary DNA Sequence of Serum Amyloid P Component," The Journal of Biological Chemistry, 260(24):13384-13388 (1985).
Wynn, T. A., "IL-13 Effector Functions," Annu Rev Immunol., 2:425-456 (2003).
Yang, L., et al., "Identification of Fibrocytes in Postburn Hypertrophic Scar," Wound Repair and Regeneration, 13(4):398-404 (2005).
Yang, L., et al., "Peripheral Blood Fibrocytes From Burn Patients: Identification and Quantification of Fibrocytes in Adherent Cells Cultured From Peripheral Blood Mononuclear Cells," Laboratory Investigation, 82(9):1183-1192 (2002).
Yu, L., et al., "Therapeutic Strategies to Halt Renal Fibrosis," Current Opinion in Pharmacology, 2:177-181 (2002).
Zahedi K., "Characterization of the Binding of Serum Amyloid P to Type IV Collagen," The Journal of Biological Chemistry, 271(25):14897-14902 (1996).
Zahedi, K., "Characterization of the Binding of Serum Amyloid P to Laminin," The Journal of Biological Chemistry, 272(4):2143-2148 (1997).
Zhang, R., et al., "C-reactive Protein Impairs Human CD14(+) Monocyte-Derived Dendritic Cell Differentiation, Maturation and Function," European Journal of Immunology, 36(11):2993-3006 (2006).
Zheng, J., et al., "Piceatannol, a Stilbene Phytochemical, Inhibits Mitochondrial FOF1-ATPase Activity by Targeting the FI Complex," Biochemical and Biophysical Research Communications, 261(2):499-503 (1999).
Barabino and Dana, "Animal Models of Dry Eye: A Critical Assessment of Opportunities and Limitations," Investigative Ophthalmology & Visual Science, vol. 45(6): 1641-1646 (2004).
Brasil et al., "Tear film analysis and its relation with palpebral fissure height and exophthalmos in Graves' ophthalmopathy," Arquivos Brasileiros de Oftalmologia, vol. 58(5): 615-618 (2005). (Abstract).
Garcia de Frutos et al., "Serum Amyloid P Component Binding to C4b-binding Protein," The Journal of Biological Chemistry: 270(45):26950-26955 (1995).
Hogaboam et al., "Chronic Airway Hyperreactivity, Goblet Cell Hyperplasia, and Peribronchial Fibrosis during Allergic Airway Disease Induced by Aspergillus fumigatus," American Journal of Pathology, vol. 156(2), pp. 723-732 (2000).
Illum, Lisbeth, "Nasal Drug Delivery-possibilities, problems and solutions," Journal of Controlled Release, vol. 87(1-3):187-198 (2003).
Kawashima et al., Pulmonary delivery of insulin with nebulized DL-lactide/glycolide copolymer (PLGA) nanospheres to prolong hypoglycemic effect, Journal of Controlled Release, vol. 62(1-2): 279-287 (1999).
Moreira et al., "Serum amyloid P attenuates M2 macrophage activation and protects against fungal spore-induced allergic airway disease," Journal of Allergy and Clinical Immunology, vol. 126(4), pp. 712-721 (2010).
Rudinger, J., "Characteristics of the amino acids as components of a peptide hormone sequence," Peptide Hormones:1-7 (1975).
Samarasinghe et al., "A comparison between intratracheal and inhalation delivery of Aspergillus fumigatus conidia in the development of fungal allergic asthma in C57BL/6 mice," Fungal Biology, vol. 115: 21-29 (2011).
Schrader et al., "Animal models of dry eye," Developments in ophthalmology, vol. 41: 298-312 (2008). (Abstract).
Sen et al., "Structural, quantitative and functional comparison of amyloid P component in sera from patients with system lupus erythematosus and healthy donors," Scandinavian Journal of Immunology, vol. 56: 645-651 (2002).
Supplementary EP Search Report No. EP 10 78 4210 dated Oct. 24, 2012.
Tennent et al., "Macrophage dependent elimination of amyloid following treatment with anti-SAP antibody," Amyloid: The International Journal of Experimental and Clinical Investigation, vol. 17(1); p. 51 (2010).
International Search Report, PCTUS/2010/037542, dated Sep. 9, 2010 (4 pages).
Written Opinion, PCTUS/2010/037542, dated Sep. 9, 2010 (7 pages).
Supplementary EP Search Report No. EP 10 78 4210, dated Oct. 24, 2012 (3 pages).
EP Search Opinion (EPO Form 1703 01.91 TRI) Application No. EP 10 78 4210, dated Oct. 24, 2012 (3 pages).

* cited by examiner

SEQUENCE LISTING

```
<160> NUMBER OF SEQ ID NOS: 4

<210> SEQ ID NO 1
<211> LENGTH: 204
<212> TYPE: PRT
<213> ORGANISM: Homo sapiens

<400> SEQUENCE: 1

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60

Lys Glu Arg Val Gly Glu Tyr Ser Leu Tyr Ile Gly Arg His Lys Val
65                  70                  75                  80

Thr Ser Lys Val Ile Glu Lys Phe Pro Ala Pro Val His Ile Cys Val
                85                  90                  95

Ser Trp Glu Ser Ser Ser Gly Ile Ala Glu Phe Trp Ile Asn Gly Thr
            100                 105                 110

Pro Leu Val Lys Lys Gly Leu Arg Gln Gly Tyr Phe Val Glu Ala Gln
        115                 120                 125

Pro Lys Ile Val Leu Gly Gln Glu Gln Asp Ser Tyr Gly Gly Lys Phe
    130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val
        195                 200

<210> SEQ ID NO 2
<211> LENGTH: 208
<212> TYPE: PRT
<213> ORGANISM: Gallus gallus
```

<400> SEQUENCE: 2

Gln Glu Asp Leu Tyr Arg Lys Val Phe Val Phe Arg Glu Asp Pro Ser
1               5                   10                  15

Asp Ala Tyr Val Leu Leu Gln Val Gln Leu Glu Arg Pro Leu Leu Asn
            20                  25                  30

Phe Thr Val Cys Leu Arg Ser Tyr Thr Asp Leu Thr Arg Pro His Ser
        35                  40                  45

Leu Phe Ser Tyr Ala Thr Lys Ala Gln Asp Asn Glu Ile Leu Leu Phe
    50                  55                  60

Lys Pro Lys Pro Gly Glu Tyr Arg Phe Tyr Val Gly Lys Tyr Val
65                  70                  75                  80

Thr Phe Arg Val Pro Glu Asn Arg Gly Glu Trp Glu His Val Cys Ala
            85                  90                  95

Ser Trp Glu Ser Gly Ser Gly Ile Ala Glu Phe Trp Leu Asn Gly Arg
        100                 105                 110

Pro Trp Pro Arg Lys Gly Leu Gln Lys Gly Tyr Glu Val Gly Asn Glu
    115                 120                 125

Ala Val Val Met Leu Gly Gln Glu Gln Asp Ala Tyr Gly Gly Gly Phe
    130                 135                 140

Asp Val Tyr Asn Ser Phe Thr Gly Glu Met Ala Asp Val His Leu Trp
145                 150                 155                 160

Asp Ala Gly Leu Ser Pro Asp Lys Met Arg Ser Ala Tyr Leu Ala Leu
            165                 170                 175

Arg Leu Pro Pro Ala Pro Leu Ala Trp Gly Arg Leu Arg Tyr Glu Ala
            180                 185                 190

Lys Gly Asp Val Val Lys Pro Arg Leu Arg Glu Ala Leu Gly Ala
    195                 200                 205

<210> SEQ ID NO 3
<211> LENGTH: 205
<212> TYPE: PRT
<213> ORGANISM: Bos taurus

<400> SEQUENCE: 3

Gln Thr Asp Leu Arg Gly Lys Val Phe Val Phe Pro Arg Glu Ser Ser
1               5                   10                  15

Thr Asp His Val Thr Leu Ile Thr Lys Leu Glu Lys Pro Leu Lys Asn
            20                  25                  30

Leu Thr Leu Cys Leu Arg Ala Tyr Ser Asp Leu Ser Arg Gly Tyr Ser
        35                  40                  45

Leu Phe Ser Tyr Asn Ile His Ser Lys Asp Asn Glu Leu Leu Val Phe
    50                  55                  60

Lys Asn Gly Ile Gly Glu Tyr Ser Leu Tyr Ile Gly Lys Thr Lys Val
65                  70                  75                  80

Thr Val Arg Ala Thr Glu Lys Phe Pro Ser Pro Val His Ile Cys Thr
            85                  90                  95

Ser Trp Glu Ser Ser Thr Gly Ile Ala Glu Phe Trp Ile Asn Gly Lys
        100                 105                 110

Pro Leu Val Lys Arg Gly Leu Lys Gln Gly Tyr Ala Val Gly Ala His
    115                 120                 125

Pro Lys Ile Val Leu Gly Gln Glu Gln Asp Ser Tyr Gly Gly Gly Phe
    130                 135                 140

Asp Lys Asn Gln Ser Phe Met Gly Glu Ile Gly Asp Leu Tyr Met Trp
145                 150                 155                 160

```
Asp Ser Val Leu Ser Pro Glu Glu Ile Leu Leu Val Tyr Gln Gly Ser
            165                 170                 175

Ser Ser Ile Ser Pro Thr Ile Leu Asp Trp Gln Ala Leu Lys Tyr Glu
            180                 185                 190

Ile Lys Gly Tyr Val Ile Val Lys Pro Met Val Trp Gly
        195                 200                 205

<210> SEQ ID NO 4
<211> LENGTH: 204
<212> TYPE: PRT
<213> ORGANISM: Cricetulus migratorius

<400> SEQUENCE: 4

Gln Thr Asp Leu Thr Gly Lys Val Phe Val Phe Pro Arg Glu Ser Glu
1               5                   10                  15

Ser Asp Tyr Val Lys Leu Ile Pro Arg Leu Glu Lys Pro Leu Glu Asn
            20                  25                  30

Phe Thr Leu Cys Phe Arg Thr Tyr Thr Asp Leu Ser Arg Pro His Ser
        35                  40                  45

Leu Phe Ser Tyr Asn Thr Lys Asn Lys Asp Asn Glu Leu Leu Ile Tyr
    50                  55                  60

Lys Glu Arg Met Gly Glu Tyr Gly Leu Tyr Ile Glu Asn Val Gly Ala
65                  70                  75                  80

Ile Val Arg Gly Val Glu Glu Phe Ala Ser Pro Val His Phe Cys Thr
                85                  90                  95

Ser Trp Glu Ser Ser Ser Gly Ile Ala Asp Phe Trp Val Asn Gly Ile
            100                 105                 110

Pro Trp Val Lys Lys Gly Leu Lys Lys Gly Tyr Thr Val Lys Thr Gln
        115                 120                 125

Pro Ser Ile Ile Leu Gly Gln Glu Gln Asp Asn Tyr Gly Gly Gly Phe
    130                 135                 140

Asp Lys Ser Gln Ser Phe Val Gly Glu Met Gly Asp Leu Asn Met Trp
145                 150                 155                 160

Asp Ser Val Leu Thr Pro Glu Glu Ile Lys Ser Val Tyr Glu Gly Ser
            165                 170                 175

Trp Leu Glu Pro Asn Ile Leu Asp Trp Arg Ala Leu Asn Tyr Glu Met
        180                 185                 190

Ser Gly Tyr Ala Val Ile Arg Pro Arg Val Trp His
    195                 200
```

SERUM AMYLOID P DERIVATIVES AND THEIR PREPARATION AND USE

CROSS-REFERENCE TO RELATED APPLICATIONS

This application claims the benefit of U.S. Provisional Application Ser. No. 61/217,931 filed on Jun. 4, 2009. All of the teachings of the above-referenced application are incorporated herein by reference.

SEQUENCE LISTING

The instant application contains a Sequence Listing which has been submitted via EFS-Web and is hereby incorporated by reference in its entirety. Said ASCII copy, created on Jun. 3, 2010, is named 1041120020.txt, and is 7,550 bytes in size.

BACKGROUND OF THE INVENTION

Serum Amyloid P(SAP) is a member of the pentraxin family of proteins. SAP is secreted by the liver and circulates in the blood as a stable pentamer. Previous research demonstrates SAP has an important role in both the initiation and resolution phases of the immune response. SAP can bind to sugar residues on the surface of bacteria and thereby promote their opsonization and engulfment by antigen-presenting cells. SAP also binds to free DNA and chromatin generated by apoptotic cells at the resolution of an immune response, thus preventing a secondary inflammatory response against these antigens. Molecules bound by SAP are removed from extracellular areas due to the ability of SAP to bind to all three classical Fcγ. receptors (FcγR), having a particular affinity for FcγRII (CD32) and FcγRIII (CD16). After receptor binding, SAP and any attached complex are generally internalized and processed by the cell.

Recently, it has been suggested that SAP can be used as a therapeutic agent to treat various disorders, including fibrosis-related disorders, hypersensitivity disorders, autoimmune disorders, mucositis, and inflammatory disorders such as those cause by microbial infection. See, for example, U.S. patent application Ser. Nos. 11/707,333, 12/217,617, 12/720,845, and 12/720,847. Protein therapeutics for treating human disease have revolutionized the health care industry. However, there are many difficulties in producing a protein therapeutic having the necessary potency and/or in sufficient quantity to be useful as a therapeutic agent. Many potential therapeutic agents are modified to increase their biological activity, such as plasma half-life, relative to the naturally-derived protein. Recombinant expression technology is usually implemented to produce polypeptides in sufficient quantity. Unfortunately, many recombinant systems produce polypeptides having different biological properties than the naturally-derived forms, which may affect the pharmacokinetics, safety, and efficacy of a therapeutic product.

Therefore, a need remains for developing SAP polypeptides, and methods of manufacturing them, suitable for therapeutic treatment of humans.

SUMMARY OF THE INVENTION

In part, the disclosure provides variant Serum Amyloid P(SAP) polypeptides and methods for producing them. The present invention includes methods and compositions for in vitro and in vivo addition, deletion, or modification of sugar residues to produce variant SAP polypeptides having a desired glycosylation pattern.

In certain aspects, the disclosure provides a glycosylated human SAP polypeptide, comprising an N-linked or O-linked oligosaccharide chain that has at least one branch terminating with a α-2,3-linked sialic acid moiety.

In certain aspects, the disclosure provides a glycosylated human SAP polypeptide, comprising an N-linked or O-linked oligosaccharide chain that has at least 50% fewer α-2,6-linked sialic acid moieties than wild-type SAP isolated from human serum.

In certain aspects, the disclosure provides methods of making a glycosylated human SAP polypeptide, comprising expressing a SAP polypeptide in a cell and isolating the SAP polypeptide from the cell. In a preferred embodiment, the cell is a CHO cell. In certain aspects, the cell is a CHO—S cell.

In certain aspects, the disclosure provides methods of making a human SAP polypeptide, comprising expressing a human SAP polypeptide in a CHO cell and isolating the human SAP polypeptide from the cell.

In certain aspects, the disclosure provides methods of making a human SAP polypeptide, comprising providing a glycosylated human SAP polypeptide containing an N-linked or O-linked oligosaccharide chain and enzymatically or chemically altering the N-linked or O-linked oligosaccharide chain of the SAP polypeptide to produce a modified glycosylated SAP polypeptide.

In certain aspects, the disclosure provides methods of making a human SAP polypeptide, comprising providing a human SAP polypeptide and enzymatically or chemically altering the SAP polypeptide to produce a glycosylated SAP polypeptide comprising an N-linked or O-linked oligosaccharide.

In certain aspects, the disclosure provides a human SAP polypeptide prepared by a process comprising expressing a SAP polypeptide in a CHO cell and isolating the SAP polypeptide from the cell.

In certain aspects, the disclosure provides a CHO cell that contains a human SAP polypeptide with an N-linked oligosaccharide chain having at least one branch of the oligosaccharide chain terminating with a α-2,3-linked sialic acid moiety.

In certain aspects, the disclosure provides a CHO cell containing a polynucleotide sequence encoding a human SAP polypeptide.

In certain aspects, the disclosure provides a human SAP polypeptide having an $IC_{50}$ for inhibiting the differentiation of monocytes into fibrocytes in vitro that is less than one-half, less than one-third, less than one-fourth, less than one-tenth, or less than one-hundredth than that of a corresponding sample of wild-type SAP isolated from human serum.

In preferred embodiments, human SAP polypeptides of the invention have an N-linked oligosaccharide chain. In some embodiments, at least one branch of the N-linked oligosaccharide chain terminates with a α-2,3-linked sialic acid moiety. In some embodiments, the N-linked oligosaccharide chain has at least 50% fewer α-2,6-linked sialic acid moieties than a wild-type SAP isolated from human serum. In some embodiments, all branches of the N-linked oligosaccharide chain terminate with α-2,3-linked sialic acid moieties. In some embodiments, the N-linked oligosaccharide chain is substantially free of α-2,6-linked sialic acid moieties. Glycovariant SAP polypeptides of the invention may comprise one or more branches, e.g., the N-linked oligosaccharide chain may be characterized as having a bi-antennary, tri-antennary, tetra-antennary, or a penta-antennary structure. In some embodiments, the N-linked oligosaccharide chain comprises a pentasaccharide core of Man[α1,6-)-(Man(α-1,3)]-Man (β1,4)-GlcNAc(β1,4)-GlcNAc(β1,N)-Asn. In some embodiments, the N-linked oligosaccharide chain comprises at least one branch having the structure NeuNAc2α3Galβ4GlcNAcβ2Manα6. In some embodiments, at least one branch of the N-linked oligosaccharide chain is substantially free of galactose and N-acetylglucosamine. In some embodiments, all the branches of the N-linked oligosaccharide chain are substantially free of galactose and N-acetylglucosamine. In some embodiments, at least one branch of the N-linked oligosaccharide chain comprises one or more mannose residues. In some embodiments, the N-linked oligosaccharide chain comprises at least one fucose residue. Any of the glycovariant SAP polypeptides of the invention may comprise at least one modified glycosyl residue. A modified glycosyl residue may be conjugated to one or more modifying groups selected from water-soluble and -insoluble polymers, therapeutic moieties, diagnostic agents, and biomolecules.

In certain aspects, the SAP polypeptide of the invention may be a recombinant polypeptide. SAP polypeptide of the invention may comprise an amino acid sequence at least 85%, 90%, 95%, 96%, 97%, 98%, 99% or 100% identical to SEQ ID Nos. 1, 2, 3, or 4. Preferably, the SAP polypeptide is a human SAP protein. A human SAP polypeptide of the invention may comprise an amino acid sequence at least 85%, 90%, 95%, 96%, 97%, 98%, 99% or 100% identical to SEQ ID NO: 1.

In certain aspects, the human SAP polypeptide of the invention is a fusion protein comprising an SAP domain and one or more heterologous domains. The heterologous domain may enhance one or more of in vivo stability, in vivo half-life, uptake/administration, tissue localization or distribution, formation of protein complexes, and/or purification.

In certain aspects, the human SAP polypeptide of the invention comprises one or more modified amino acid residues, e.g., a PEGylated amino acid, a glycosylated (e.g., O-linked glycosylation) amino acid, a prenylated amino acid, an acetylated amino acid, a biotinylated amino acid, and/or an amino acid conjugated to an organic derivatizing agent. The modified amino acid residues may enhance one or more of in vivo stability, in vivo half-life, uptake/administration, tissue localization or distribution, formation of protein complexes, and/or purification.

In preferred embodiments, human SAP polypeptides of the invention have increased biological activity relative to a corresponding sample of wild-type SAP isolated from human serum. In certain aspects, the SAP polypeptides of the invention have an $IC_{50}$ for inhibiting the differentiation of monocytes into fibrocytes in vitro that is less than one-half, less than one-third, less than one-fourth, less than one-tenth, or less than one-hundredth that of a corresponding sample of wild-type SAP isolated from human serum.

In certain aspects, methods of making any of the human SAP polypeptides of the invention comprise an additional step of enzymatically or chemically altering the SAP polypeptide to attach an N-linked or O-linked oligosaccharide chain to the SAP polypeptide or to modify the existing N-linked or O-linked oligosaccharide chain of the SAP polypeptide. In some embodiments, enzymatically or chemically altering the SAP polypeptide comprises treating the SAP polypeptide with one or more enzymatic proteins selected from glycosyltransferases, glycosidases, and phosphatases. In some embodiments, the process of enzymatically or chemically altering the SAP polypeptide is effected in the presence of one or more sugar precursors. Suitable sugar precursors include, but are not limited to, UDP-N-acetylglucosamine, CMP-N-glycolylneuraminic acid UDP-N-acetylgalactosamine, CMP-N-acetylneuraminic acid, UDP-galactose, and GDP-fucose. In some embodiments, the process of enzymatically or chemically altering the SAP polypeptide removes one or more terminal α-2,6-linked sialic acid moieties from the N-linked or O-linked oligosaccharide chain. In some embodiments, the process of enzymatically or chemically altering the isolated SAP polypeptide replaces one or more terminal α-2,6-linked sialic acid moieties on the oligosaccharide chain with one or more α-2,3-linked sialic acid moieties.

The disclosure further provides pharmaceutical preparations of human SAP polypeptides of the invention suitable for use in a mammal. Pharmaceutical preparations of the invention include at least one of the SAP polypeptides disclosed herein and a pharmaceutically acceptable carrier. In some embodiments, the pharmaceutical preparation further comprises an additional active agent. In some embodiments, the pharmaceutical preparation is prepared as a sustained release formulation. In some embodiments, pharmaceutical preparations of the disclosure are suitable for administration to a patient topically, by injection, by intravenous injection, by inhalation, by continuous depot, or by pump.

The disclosure further provides methods for treating or preventing SAP-responsive disorders or conditions by administering to a patient in need thereof a therapeutically effective amount of one or more of the SAP polypeptides of the invention. SAP-responsive disorders or conditions include, but are not limited to, fibrotic or fibroproliferative disorders or conditions, hypersensitivity disorders or conditions, autoimmune disorders or conditions, inflammatory diseases or conditions, and mucositis. The SAP polypeptide of the invention may be administered to a patient topically, by injection, by intravenous injection, by inhalation, by continuous depot or pump, or a combination thereof. In some embodiments, the SAP polypeptide of the invention is administered with one or more additional active agents.

BRIEF DESCRIPTIONS OF THE DRAWINGS

FIG. 1. Fibrocyte differentiation assay. An ELISA-based assay was used to measure production of MDC after incubation of monocytes with SAP polypeptides. The Y-axis indicates the average potency (i.e., average of 7 independent experiments) of human serum-derived SAP (hSAP) compared to recombinant human SAP (rhSAP) isolated from CHO—S cells. Relative activity of hSAP is set at 1.0.

FIG. 2. Glycan structural analysis of variant SAP polypeptides. Liquid Chromatography Mass Spectrometry (LCMS) analysis (A) and Anion-Exchange High Performance Liquid Chromatography (AEX-HPLC) analysis (B) was used to determine the sialic acid linkages on glycoremodeled recombinant human SAP isolated from CHO—S cells. Liquid Chromatography Mass Spectrometry (LCMS) analysis (C) and Anion-Exchange High Performance Liquid Chromatography (AEX-HPLC) analysis (D) was used to determine the sialic acid linkages on glycoremodeled hSAP (human serum-derived SAP). Liquid Chromatography Mass Spectrometry (LCMS) analysis (E) and Anion-Exchange High Performance Liquid Chromatography (AEX-HPLC) analysis (F) was used to determine the sialic acid linkages on rhSAP that was treated with an α-2,3-sialyltransferase to increase the number of terminal 2,3-linked sialic acids on the SAP glycans. For LCMS figures, the X-axis represents mass in Daltons, and the Y-axis is represents relative intensity. For the HPLC traces, the X-axis is the time in minutes, and the Y-axis is absorbance units (mAU).

Figure 3:
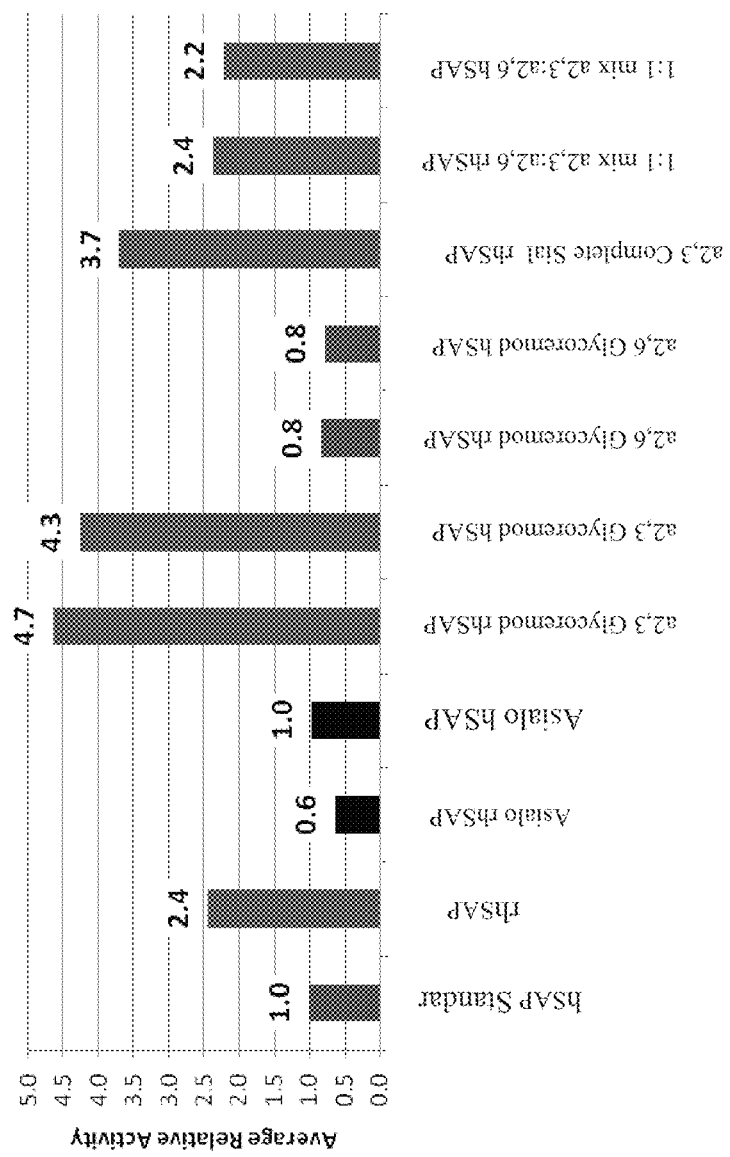

FIG. 3. Fibrocyte differentiation assay. An ELISA-based assay was used to measure production of MDC after incubation of monocytes with SAP variant polypeptides. The Y-axis indicates the average relative activity of each SAP variant compared to a hSAP reference standard, for which the activity is set at 1.0 (see the left-most bar).

Figure 4:
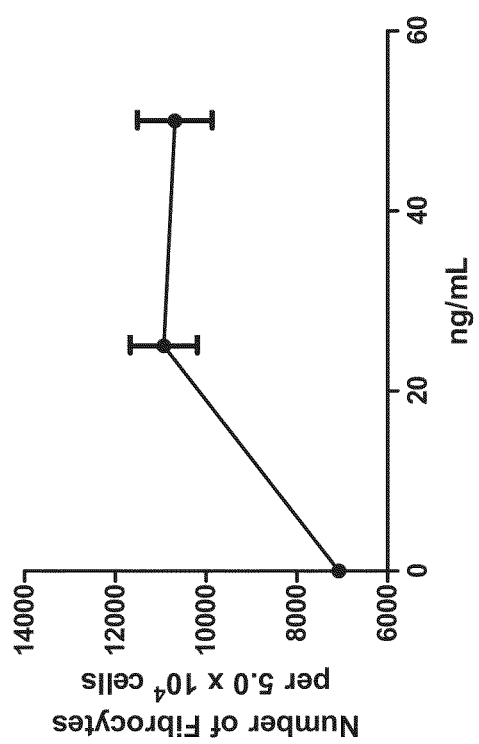

FIG. 4. Fibrocyte differentiation assay. Monocytes were treated with hMCSF and then subsequently quantified for fibrocyte differentiation. The X-axis represents the concentration of hMCSF incubated with donor monocytes. The Y-axis indicates the amount of fibrocyte proliferation at day five as measured by the enumeration of fibrocytes per $5.0 \times 10^4$ cells.

Figure 5:
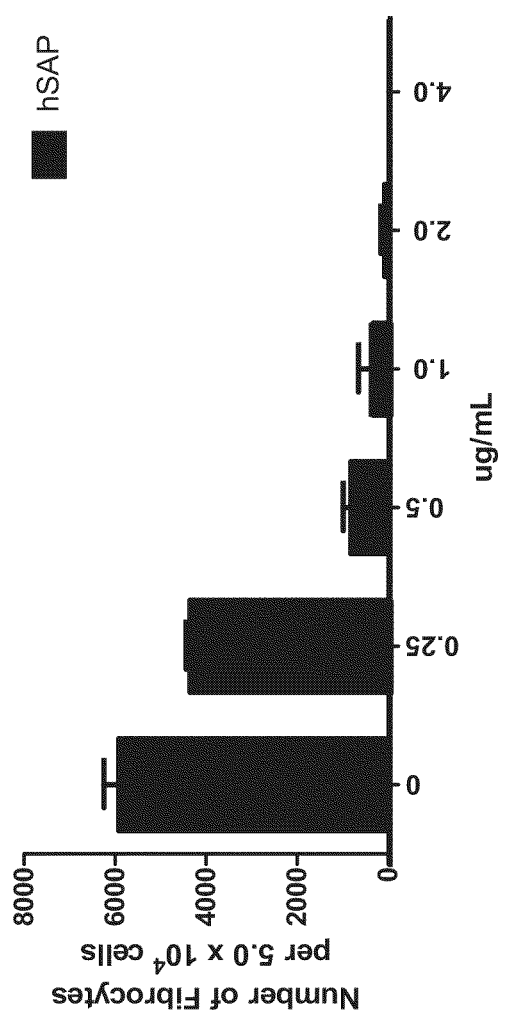

FIG. 5. Fibrocyte differentiation assay. Monocytes were treated with hSAP and then subsequently quantified for fibrocyte differentiation. The X-axis indicates the concentration of hSAP incubated with donor monocytes. The Y-axis indicates the amount of fibrocyte proliferation at day five as measured by the enumeration of fibrocytes per $5.0 \times 10^4$ cells.

DETAILED DESCRIPTION OF THE INVENTION

Overview

Most naturally occurring peptides have carbohydrate moieties (i.e., glycans) attached to the peptide via specific linkages to certain amino acids along the length of the primary peptide chain, thus forming "glycopeptides." The glycosylation pattern on any given peptide can have enormous implications for the function of that peptide. For example, the structure of the N-linked glycans on a peptide can impact various characteristics of the peptide, including protease susceptibility, intracellular trafficking, secretion, tissue targeting, biological half-life, and antigenicity. The alteration of one or more of these characteristics greatly affects the efficacy of a peptide in its natural setting.

The glycan structures found in naturally occurring glycopeptides are typically divided into two classes, N-linked and O-linked glycans. Peptides expressed in eukaryotic cells are typically N-glycosylated on asparagine residues at sites in the peptide primary structure containing the sequence asparagine-X-serine/threonine, where X can be any amino acid except proline and aspartic acid. The carbohydrate portion of such peptides is known as an N-linked glycan or N-linked oligosaccharide. The early events of N-glycosylation occur in the endoplasmic reticulum (ER) and are conserved in mammals, plants, insects and other higher eukaryotes. First, an oligosaccharide chain comprising fourteen sugar residues is constructed on a lipid carrier molecule. As the nascent peptide is translated and translocated into the ER, the entire oligosaccharide chain is transferred to the amide group of the asparagine residue in a reaction catalyzed by a membrane-bound glycosyltransferase enzyme. The N-linked glycan is further processed both in the ER and in the Golgi apparatus. The further processing generally entails removal of some of the sugar residues and addition of other sugar residues in reactions catalyzed by glycosylases and glycosyltransferases specific for the sugar residues removed and added.

Typically, the final structures of the N-linked glycans are dependent upon the organism in which the peptide is produced. For example, peptides produced in bacteria are generally unglycosylated. Peptides expressed in insect cells typically contain high mannose or pauci-mannose N-linked oligosaccharide chains. Peptides produced in mammalian cell culture are usually differentially glycosylated depending upon the species and cell culture conditions. Even in the same species and under the same conditions, a certain amount of heterogeneity in the glycosyl chain is sometimes encountered. In general, peptides produced in plant cells comprise glycan structures that differ significantly from those produced in animal cells.

A variety of methods have been proposed in the art to customize the glycosylation pattern of a peptide, including methods described in the Published International Applications Nos. WO 99/22764, WO 98/58964, and WO 99/54342 as well as in U.S. Pat. No. 5,047,335. Essentially, many of the enzymes required for the in vitro glycosylation of peptides have been cloned and sequenced. In some instances, these enzymes have been used in vitro to add specific sugars to a glycan on a peptide. In other instances, cells have been genetically engineered to express a combination of enzymes and desired peptides such that addition of a desired sugar moiety to an expressed peptide occurs within the cell.

Two principal classes of enzymes are used in the synthesis of carbohydrates: glycosyltransferases and glycosidases. Glycosyltransferases add or modify the existing oligosaccharide structures on a peptide. Glycosyltransferases are effective for producing specific products with good stereochemical and regiochemical control. Glycosyltransferases have been used to prepare oligosaccharides and to modify terminal N- and O-linked carbohydrate structures, particularly on peptides produced in mammalian cells. For example, the terminal oligosaccharides of glycopeptides can be completely sialylated and/or fucosylated to provide more consistent sugar structures using glycosyltransferases, which may improves glycopeptide pharmacodynamics and a variety of other biological properties.

The glycosidases are further classified as exoglycosidases (e.g., β-mannosidase, β-glucosidase), and endoglycosidases (e.g. Endo-A, Endo-M). Glycosidases normally catalyze the hydrolysis of a glycosidic bond. However, under appropriate conditions, they can be used to form this linkage. Most glycosidases used for carbohydrate synthesis are exoglycosidases; the glycosyl transfer occurs at the non-reducing terminus of the substrate. The glycosidase binds a glycosyl donor in a glycosyl-enzyme intermediate that is either intercepted by water to yield the hydrolysis product, or by an acceptor, to generate a new glycoside or oligosaccharide. An exemplary pathway using an exoglycosidase is the synthesis of the core trisaccharide of all N-linked glycopeptides, including the β-mannoside linkage, which is formed by the action of β-mannosidase (Singh et al., Chem. Commun. 993-994 (1996)). Although their use is less common than that of the exoglycosidases, endoglycosidases are also utilized to prepare carbohydrates. Endoglycosidases can be used to transfer an entire oligosaccharide chain, rather than a monosaccharide, onto a polypeptide. Oligosaccharide fragments have been added to substrates using endo-β-N-acetylglucosamines, such as endo-F and endo-M (Wang et al., Tetrahedron Lett. 37: 1975-1978; and Haneda et al., Carbohydr. Res. 292: 61-70 (1996). Each of these classes of enzymes has been successfully used produce glycosylated peptides. For a general review, see, Crout et al., Curr. Opin. Chem. Biol. 2: 98-111 (1998).

Serum amyloid P (SAP) is a naturally occurring serum protein in mammals composed of five identical subunits, or "promoters", which are non-covalently associated in a disk-like complex. SAP belongs to the pentraxin super family of proteins, which are characterized by this cyclic pentameric structure. The classical short pentraxins include SAP as well as C-reactive protein (Osmand, A. P., et al., Proc. Nat. Acad. Sci., 74: 739-743, 1997). SAP is normally synthesized in the liver and has a physiological half-life of twenty-four hours. The sequence of the human SAP subunit is disclosed below, which corresponds to amino acids 20-223 of Gene bank Accession NO. NP_001630 (signal sequence not depicted).

(SEQ ID NO: 1)
HTDLSGKVFVFPRESVTDHVNLITPLEKPLQNFTLCFRAYSDLSRAYSLF

SYNTQGRDNELLVYKERVGEYSLYIGRHKVTSKVIEKFPAPVHICVSWES

SSGIAEFWINGTPLVKKGLRQGYFVEAQPKIVLGQEQDSYGGKFDRSQSF

VGEIGDLYMWDSVLPPENILSAYQGTPLPANILDWQALNYEIRGYVIIKP

LVWV

The sequence of the *Gallus gallus* SAP subunit is disclosed below.

(SEQ ID NO: 2)
QEDLYRKVFVFREDPSDAYVLLQVQLERPLLNFTVCLRSYTDLTRPHSLF

SYATKAQDNEILLFKPKPGEYRFYVGGKYVTFRVPENRGEWEHVCASWE

SGSGIAEFWLNGRPWPRKGLQKGYEVGNEAVVMLGQEQDAYGGGFDVY

NSFTGEMADVHLWDAGLSPDKMRSAYLALRLPPAPLAWGRLRYEAKGD

VVVKPRLREALGA

The sequence of the *Bos taurus* SAP subunit is disclosed below.

(SEQ ID NO: 3)
QTDLRGKVFVFPRESSTDHVTLITKLEKPLKNLTLCLRAYSDLSRGYSLF

SYNIHSKDNELLVFKNGIGEYSLYIGKTKVTVRATEKFPSPVHICTSWES

STGIAEFWINGKPLVKRGLKQGYAVGAHPKIVLGQEQDSYGGGFDKNQSF

MGEIGDLYMWDSVLSPEEILLVYQGSSSISPTILDWQALKYEIKGYVIVK

PMVWG

The sequence of the *Cricetulus migratorius* SAP subunit is disclosed below.

(SEQ ID NO: 4)
QTDLTGKVFVFPRESESDYVKLIPRLEKPLENFTLCFRTYTDLSRPHSLF

SYNTKNKDNELLIYKERMGEYGLYIENVGAIVRGVEEFASPVHFCTSWES

SSGIADFWVNGIPWVKKGLKKGYTVKTQPSIILGQEQDNYGGGFDKSQSF

VGEMGDLNMWDSVLTPEEIKSVYEGSWLEPNILDWRALNYEMSGYAVIRP

RVWH

One aspect of the present invention relates to the surprising discovery that modification of a glycan structure on a human SAP polypeptide can increase the biological activity of the SAP polypeptide relative to a corresponding sample of wild-type SAP isolated from human serum. As demonstrated by the examples of the disclosure, isolated SAP from human serum contains only α-2,6-linked sialic acid residues. In contrast, recombinant human SAP produced in CHO cells contains only α-2,3-linked sialic acid residues. Using in vitro cell-based bioassays, α-2,3-linked sialic acid SAP polypeptides were demonstrated to have consistently higher activity than wild-type SAP (i.e., SAP comprising α-2,6-linked sialic acid moieties) isolated from human serum. The variant SAP polypeptides of the invention would be more effective as therapeutic agents due to their increased biological potency. For example, more potent SAP variants may require lower dosing and/or less frequent dosing relative to wild-type SAP isolated from human serum. The present disclosure provides both variant human SAP polypeptides and methods for making the same. In particular, the disclosure includes methods and compositions for in vitro and in vivo addition, deletion, or modification of sugar residues to produce a human SAP polypeptide having a desired glycosylation pattern.

Definitions

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and nucleic acid chemistry and hybridization are those well known and commonly employed in the art. Standard techniques are used for nucleic acid and peptide synthesis. The techniques and procedures are generally performed according to conventional methods in the art and various general references (e.g., Sambrook et al., 1989, Molecular Cloning: A Laboratory Manual, 2d ed. Cold Spring Harbor Laboratory Press, Cold Spring Harbor, N.Y.), which are provided throughout this document.

The articles "a" and "an" are used herein to refer to one or to more than one (i.e., to at least one) of the grammatical object of the article. By way of example, "an element" means one element or more than one element.

As used herein, the terms "treatment" and "treating", refer to obtaining a desired pharmacologic and/or physiologic effect. The effect may be prophylactic in terms of completely or partially preventing a disorder or symptom thereof and/or may be therapeutic in terms of a partial or complete cure for a disorder and/or adverse affect attributable to the disorder. "Treatment", as used herein, covers any treatment of a disease in a mammal, particularly in a human, and includes: (a) increasing survival time; (b) decreasing the risk of death due to the disease; (c) inhibiting the disease, i.e., arresting its development or reducing the rate of disease progression; and (d) relieving the disease, i.e., causing regression of the disease.

As used herein, a therapeutic that "inhibits" or "prevents" a disorder or condition is a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein the terms "subject" and "patient" refer to animals including mammals, such as humans. The term "mammal" includes primates, domesticated animals including dogs, cats, sheep, cattle, horses, goats, pigs, mice, rats, rabbits, guinea pigs, captive animals such as zoo animals, and wild animals.

As used herein the term "tissue" refers to an organ or set of specialized cells such as skin tissue, lung tissue, kidney tissue, and other types of cells.

The term "therapeutic effect" is art-recognized and refers to a local or systemic effect in animals, particularly mammals, and more particularly humans caused by a pharmacologically active substance. The phrase "therapeutically effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration, which can readily be determined by one of ordinary skill in the art. For example, certain compositions described herein may be administered in a sufficient amount to produce a desired effect at a reasonable benefit/risk ratio applicable to such treatment.

As used herein, the term "nucleic acid" refers to a polynucleotide such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotide.

The terms "peptides", "proteins" and "polypeptides" are used interchangeably herein. The term "purified protein" refers to a preparation of a protein or proteins that are preferably isolated from, or otherwise substantially free of, other proteins normally associated with the protein(s) in a cell or cell lysate. The term "substantially free of other cellular proteins" or "substantially free of other contaminating proteins" is defined as encompassing individual preparations of each of the proteins comprising less than 20% (by dry weight) contaminating protein, and preferably comprises less than 5% contaminating protein. Functional forms of each of the proteins can be prepared as purified preparations by using a cloned gene as is well known in the art. By "purified", it is meant that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 85% by weight, more preferably 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

"N-linked" oligosaccharides are those oligosaccharides that are linked to a peptide backbone through asparagine, by way of an asparagine-N-acetylglucosamine linkage. N-linked oligosaccharides are also called "N-glycans." Naturally occurring N-linked oligosaccharides have a common pentasaccharide core of Man[($\alpha$-1,6-)-(Man($\alpha$-1,3)]-Man ($\beta$1,4)-GlcNAc($\beta$1,4)-GlcNAc($\beta$1,N). They differ in the presence of, and in the number of branches (also called antennae) of peripheral sugars such as N-acetylglucosamine, galactose, N-acetylgalactosamine, fucose, and sialic acid. Optionally, this structure may also contain a core fucose molecule and/or a xylose molecule.

The term "sialic acid" refers to any member of a family of nine-carbon carboxylated sugars. The most common member of the sialic acid family is N-acetyl-neuraminic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) J. Biol. Chem. 261: 11550-11557; Kanamori et al., J. Biol. Chem. 265: 21811-21819 (1990)). Also included are 9-substituted sialic acids such as a 9-O—$C_1C_6$-acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, Glycobiology 2: 25-40 (1992); Sialic Acids: Chemistry, Metabolism and Function, R. Schauer, Ed. (Springer-Verlag, New York (1992)).

A "genetically engineered" or "recombinant" cell is a cell having one or more modifications to the genetic material of the cell. Such modifications include, but are not limited to, insertions of genetic material, deletions of genetic material and insertion of genetic material that is extrachromosomal whether such material is stably maintained or not.

As used herein, the term "modified sugar," refers to a naturally- or non-naturally-occurring carbohydrate that is enzymatically added onto an amino acid or a glycosyl residue of a peptide in a process of the invention. The modified sugar is selected from a number of enzyme substrates including, but not limited to, sugar nucleotides (mono-, di-, and tri-phosphates), activated sugars (e.g., glycosyl halides, glycosyl mesylates) and sugars that are neither activated nor nucleotides. A "modified sugar" maybe covalently functionalized with a "modifying group." Useful modifying groups include, but are not limited to, water-soluble and -insoluble polymers, therapeutic moieties, diagnostic moieties, biomolecules. The locus of functionalization with the modifying group is selected such that it does not prevent the "modified sugar" from being added enzymatically to a peptide or glycosyl residue of the peptide.

Variant SAP Polypeptides

In part, the disclosure provides variant Serum Amyloid P (SAP) polypeptides. In particular, SAP variants of the invention include glycosylated human SAP polypeptides that comprise one or more N-linked or O-linked oligosaccharide chains each independently having one, two, three, four, five or more branches terminating with an $\alpha$-2,3-linked sialic acid moiety. In some embodiments, all the branches of the N-linked or O-linked oligosaccharide chains terminate in $\alpha$-2,3-linked moieties. Other SAP variants of the invention include glycosylated human SAP polypeptides that contain an N-linked or O-linked oligosaccharide chains having at least 20%, 25%, 30%, 35% 40%, 45%, 50%, 55%, 60%, 65% 75%, 80%, 85%, or even at least 95% fewer $\alpha$-2,6-linked sialic acid moieties than a wild-type SAP polypeptide derived from human serum. In some embodiments, the N-linked or O-linked oligosaccharide chains are substantially free of $\alpha$-2,6-linked sialic acid moieties, e.g., having less than 80%, 85%, 90%, 95%, 97%, 98% or even less than 99% $\alpha$-2,6-linked sialic acid moieties relative to a wild-type SAP polypeptide derived from human serum). Glycovariant SAP polypeptides of the invention may comprise an N-linked oligosaccharide or O-linked chain having one or more branches (e.g., having a bi-antennary, tri-antennary, tetra-antennary, penta-antennary, etc. structure). In certain embodiments, SAP polypeptides of the invention comprise an N-linked or O-linked oligosaccharide chain wherein one, two, three, four, or five branches of the oligosaccharide chain are substantially free of galactose and N-acetylglucosamine (e.g., having less than 80%, 85%, 90%, 95%, 97%, 98% or even less than 99% N-acetylglucosamine relative to a wild-type SAP polypeptide derived from human serum). Certain SAP polypeptides of the invention have N-linked or O-linked oligosaccharide chains that are substantially free of galactose and N-acetylglucosamine (e.g., having less than 80%, 85%, 90%, 95%, 97%, 98% or even less than 99% galactose and/or N-acetylglucosamine relative to a wild-type SAP polypeptide derived from human serum). In some embodiments, SAP polypeptides of the invention comprise an N-linked or O-linked oligosaccharide chain wherein one, two, three, four, or five branches of the oligosaccharide chain contain one or more mannose residues. In certain embodiments, the SAP polypeptide of the invention comprises an N-linked oligosaccharide having a pentasaccharide core of Man[($\alpha$-1,6-)-(Man($\alpha$-1,3)]-Man($\beta$1,4)-GlcNAc($\beta$1,4)-GlcNAc($\beta$1,N)-Asn. This pentasaccharide core also may comprise one or more fucose or xylose residues. In certain embodiments, SAP polypeptides of the invention comprise an N-linked oligosaccharide chain wherein one, two, three, four, or five branches of the oligosaccharide chain have the structure NeuNAc2α3Galβ4GlcNAcβ2Manα6. SAP polypeptides of the invention also may comprise an N-linked oligosaccharide chain wherein all branches have the structure NeuNAc2α3Galβ4GlcNAcβ2Manα6.

Variant SAP polypeptides of the invention may comprise one or more "modified" sugar residues. Modified sugars are substituted at any position that allows for the attachment of the modifying moiety or group. In preferred aspects, modified sugar is substituted at a position that still allows the sugar to function as a substrate for an enzyme used to couple the modified sugar to the SAP peptide. A modifying group can be attached to a sugar moiety by enzymatic means, chemical means or a combination thereof, thereby producing a modified sugar, e.g., modified galactose, fucose, or sialic acid. Modifying groups suitable for use in the present invention as well as methods for conjugating these modifying groups to sugar residues are described in the following section.

In preferred aspects, variant SAP polypeptides of the invention have an $IC_{50}$ for inhibiting the differentiation of monocytes into fibrocytes in vitro that is less than one-half that of a corresponding sample of wild-type SAP isolated from human serum. In some embodiments, variant SAP polypeptides of the invention have an $IC_{50}$ for inhibiting the differentiation of monocytes into fibrocytes in vitro that is less than 1/3, less than 1/4, less than 1/10, or less than 1/100 that of a corresponding sample of wild-type SAP isolated from human serum.

Variant SAP polypeptides of the invention may be at least 60%, at least 70%, at least 80%, at least 85%, at least 90%, at least 95%, at least 96%, at least 97%, at least 98%, at least 99%, or 100% identical to the amino acid sequence of SEQ ID NO: 1, as determined using the FASTDB computer program based on the algorithm of Brutlag et al. (Comp. App. Biosci., 6:237-245 (1990)). In a specific embodiment, parameters employed to calculate percent identity and similarity of an amino acid alignment comprise: Matrix=PAM 150, k-tuple=2, Mismatch Penalty=1, Joining Penalty=20, Randomization Group Length=0, Cutoff Score=1, Gap Penalty=5 and Gap Size Penalty=0.05.

The term "SAP polypeptide" encompasses functional fragments and fusion proteins comprising any of the preceding. Generally, an SAP polypeptide will be designed to be soluble in aqueous solutions at biologically relevant temperatures, pH levels and osmolarity. The SAP protomers that non-covalently associate together to form a pentameric SAP complex may have identical amino acid sequences and/or post-translational modifications or, alternatively, individual SAP protomers within a single complex may have different sequences and/or modifications. The term SAP polypeptide includes polypeptides comprising any naturally occurring SAP polypeptide as well as any variant thereof (including mutants, fragments, and fusions). A SAP polypeptide of the invention may be a recombinant polypeptide. In preferred embodiments, the SAP polypeptide of the invention is a human SAP polypeptide.

In some embodiments, pharmaceutical compositions are provided comprising a variant SAP polypeptide of the invention, or a functional fragment thereof. In some aspects, the amino acid sequence of a SAP variant may differ from SEQ ID NO: 1 by one or more conservative or non-conservative substitutions. As used herein, "conservative substitutions" are residues that are physically or functionally similar to the corresponding reference residues, i.e., a conservative substitution and its reference residue have similar size, shape, electric charge, and/or chemical properties (e.g., the ability to form covalent or hydrogen bonds). Preferred conservative substitutions are those fulfilling the criteria defined for an accepted point mutation in Dayhoff et al., Atlas of Protein Sequence and Structure 5:345-352 (1978 & Supp.). Examples of conservative substitutions are substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine. Additional guidance concerning which amino acid changes are likely to be phenotypically silent can be found in Bowie et al., Science 247:1306-1310 (1990).

Variant SAP polypeptides and fragments thereof that retain biological function are useful in the pharmaceutical compositions and methods described herein. In some embodiments, a variant SAP polypeptide or fragment thereof binds FcγRI, FcγRIIA, and/or FcγRIIIB. In some embodiments, a variant SAP polypeptide or fragment thereof inhibits one or more of fibrocyte, fibrocyte precursor, myofibroblast precursor, and/or hematopoietic monocyte precursor differentiation. SAP variants may be generated by modifying the structure of an SAP polypeptide for such purposes as enhancing therapeutic efficacy or stability (e.g., ex vivo shelf life and resistance to proteolytic degradation in vivo).

In certain aspects, the variant SAP polypeptides of the disclosure may further comprise post-translational modifications in addition to any that are naturally present in the SAP polypeptide. Such modifications include, but are not limited to, acetylation, carboxylation, glycosylation (e.g., O-linked oligosaccharides, N-linked oligosaccharides, etc.), phosphorylation, and lipidation. As a result, the modified SAP polypeptide may contain non-amino acid elements, such as polyethylene glycols, lipids, poly- or mono-saccharides, and phosphates.

In certain aspects, one or more modifications to the SAP polypeptide described herein may enhance the stability of the SAP polypeptide. For example, such modifications may enhance the in vivo half-life of the SAP polypeptide or reduce proteolytic degradation of the SAP polypeptide.

In certain aspects, variant SAP polypeptides of the invention include fusion proteins having at least a portion of the human SAP polypeptide and one or more fusion domains or heterologous portions. Well known examples of such fusion domains include, but are not limited to, polyhistidine, Glu-Glu, glutathione S transferase (GST), thioredoxin, protein A, protein G, and immunoglobulin heavy chain constant region (Fc), maltose binding protein (MBP), or human serum albumin A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel-, or cobalt-conjugated resins are used. As another example, a fusion domain may be selected so as to facilitate detection of the SAP polypeptides. Examples of such detection domains include the various fluorescent protein (e.g., GFP) as well as "epitope tags," which are usually short peptide sequences for which a specific antibody is available. Well known epitope tags for which specific monoclonal antibodies are readily available include FLAG, influenza virus hemagglutinin (HA) and c-myc tags. In some cases, the fusion domains have a protease cleavage site that allows the relevant protease to partially digest the fusion proteins and thereby liberate the recombinant protein therefrom. The liberated proteins can then be isolated from the fusion domain by subsequent chromatographic separation. In some cases, the SAP polypeptide may be fused to a heterologous domain that stabilizes the SAP polypeptide in vivo. By "stabilizing" is meant anything that increases serum half-life, regardless of whether this is because of decreased destruction, decreased clearance by the kidney, or other pharmacokinetic effect. Fusions with the Fc portion of an immunoglobulin and serum albumin are known to confer increased stability.

It is understood that different elements of the fusion proteins may be arranged in any manner that is consistent with the desired functionality. For example, an SAP polypeptide may be placed C-terminal to a heterologous domain, or, alternatively, a heterologous domain may be placed C-terminal to an SAP polypeptide. The SAP polypeptide and the heterologous domain need not be adjacent in a fusion protein, and additional domains or amino acid sequences (e.g., linker sequences) may be included C- or N-terminal to either domain or between the domains.

Methods of Producing Altered N-Glycosylation Molecules

Described herein are methods of producing variant human SAP polypeptides. The methods generally involve a step of contacting an SAP polypeptide with one or more chemical or enzymatic agents to produce or modify a glycosylation structure on the SAP polypeptide. The methods can be cell-based or non-cell based.

Enzymes useful for producing or modifying glycan structures are well known in the art. Most enzymes/proteins useful in the methods of the disclosure can be categorized into one of two functional classes: glycosyltransferases and glycosidases. Glycosyltransferases (e.g., N-acetylglucosaminyl-transferases, galactosyl-transferases, fucosyl-transferases, sialyl-transferases, glucosyl-transferases, mannosyl-transferases, etc.), as used herein, refers to any enzyme/protein that has the ability to transfer a donor sugar to an acceptor moiety. Glycosidases (e.g., glucosidases, mannosidases, N-acetyl-glucosaminidases, sialidases, fucosidases, etc.), as used herein, refers to any enzyme/protein that has the ability to catalyze the hydrolysis of the glycosidic linkage between sugar moieties.

Cell-based methods for producing altered glyco-forms of an SAP polypeptide use either wild-type (e.g., CHO cells) or genetically engineered cells that have at least one modified glycosylation activity relative to a human cell. Cells suitable for the methods of the disclosure include, for example, fungal cells, prokaryotic cell (i.e., bacteria, Archaea) plant cells, or animal cells (e.g., nematode, insect, plant, bird, reptile, or mammal (e.g., a mouse, rat, rabbit, hamster, gerbil, dog, cat, goat, pig, cow, horse, whale, monkey, or human)). The cells can be primary cells, immortalized cells, or transformed cells. Such cells can be obtained from a variety of commercial sources and research resource facilities, e.g., the American Type Culture Collection (Rockville, Md.). In certain aspects, the cell used for producing a variant SAP polypeptide is a CHO cell.

The term "glycosylation activity" refers to any activity that is (i) capable of adding N-linked or O-linked glycans to a target molecule (i.e., an oligosaccharyl-transferase activity); (ii) removing N-linked or O-linked glycans from a target molecule; (iii) modifying one or more N-linked or O-linked glycans on a target molecule; (iv) modifying dolichol-linked oligosaccharides; (v) capable of aiding the activity of one or more of the activities under i-iv. Accordingly, glycosylation activity includes, for example, glycosidase activity, glycosyl-transferase activity, sugar nucleotide synthesis, modification, or transporter activity. Modification of one or more N-linked or O-linked glycans on a target molecule includes the action of a mannosylphosphoryl-transferase activity, a kinase activity, or a phosphatase activity, e.g., a mannosylphosphoryl-transferase, a kinase, or a phosphatase activity that alters the phosphorylation state of glycans on target molecules.

Engineered cells useful in the methods of the disclosure may have one or more genetic modifications including, but not limited to: (i) deletion of an endogenous gene encoding a protein having glycosylation activity; (ii) introduction of a recombinant nucleic acid encoding a mutant form of a protein (e.g., endogenous or exogenous protein) having an glycosylation activity; (iii) introduction or expression of an RNA molecule that interferes with the functional expression of a protein having the glycosylation activity; (iv) introduction of a recombinant nucleic acid encoding a wild-type (e.g., endogenous or exogenous) protein having glycosylation activity; or (v) altering the promoter or enhancer elements of one or more endogenous genes encoding proteins having glycosylation activity to thus alter the expression of the encoded proteins. RNA molecules described above include, for example, small-interfering RNA (siRNA), short hairpin RNA (shRNA), anti-sense RNA, or micro RNA (miRNA). It is understood that item (ii) includes, for example, replacement of an endogenous gene (e.g., by homologous recombination) with a gene encoding a protein having greater glycosylation activity relative to the endogenous gene so replaced.

The genetically engineered cells described herein have one or more altered glycosylation activities such as: (i) an increase in one or more glycosylation activities in the genetically modified cell, (ii) a decrease in one or more glycosylation activities in the genetically modified cell, (iii) a change in the localization or intracellular distribution of one or more glycosylation activities in the genetically modified cell, or (iv) a change in the ratio of one or more glycosylation activities in the genetically modified cell relative to an unmodified cell of the same origin. It is understood that an increase in the amount of glycosylation activity can be due to overexpression of one or more proteins having glycosylation activity, an increase in copy number of an endogenous gene (e.g., gene duplication), or an alteration in the promoter, enhancer, or suppressor of an endogenous gene that stimulates an increase in expression of the protein encoded by the gene. A decrease in one or more glycosylation activities can be due to overexpression of a mutant form (e.g., a dominant negative form) of one or more proteins having glycosylation-altering activities, introduction or expression of one or more interfering RNA molecules that reduce the expression of one or more proteins having an glycosylation activity, or deletion of one or more endogenous genes that encode a protein having glycosylation activity.

Genetically engineered cells used by the methods of the disclosure can express (e.g., overexpress) wild-type or mutant genes encoding proteins having glycosylation activity. Such genes include, but are not limited to, ALG7, ALG13, ALG14, ALG1, ALG2, ALG11, RFT1, ALG3, ALG9, ALG12, ALG6, ALG8, ANL1, ALG10, ALG5, OST3, OST4, OST6, STT3, OST1, OST5, WBP1, SWP1, OST2, DPM1, SEC59, OCH1, MNN9, VAN1, MNN8, MNN10, MNN11, HOC1, MNN2, MNN5, MNN6, KTR1, YUR1, MNN4, KRE2, KTR2, KTR3, MNN1, MNS1, MNN4, PNO1, MNN9, glucosidase I, glucosidase II, or endomannosidase. Genes encoding proteins having glycosylation activity can be from any species (e.g., lower eukaryotes (e.g., fungus (including yeasts) or trypanosomes), prokaryotes (i.e., bacteria or Archaea), plant, or animal (e.g., insect, bird, reptile, or mammal, such as mouse or rat, dog, cat, horse, goat, cow, pig, non-human primate, or human). It is understood that genetically engineered cells used for the methods of the disclosure can express any number of genes (e.g., genes encoding proteins having glycosylation activity) and/or any combination of one or more (e.g., 2, 3, 4, 5, 6, 7, 8, 9 10, 11, 12, 15, or 20 or more) of any of the genes recited herein. In addition, any genetically engineered cells used by the methods of the disclosure may comprise any number of mutations that alter or abrogate one or more glycosylation activities.

In some embodiments, the term "gene expression" or "expression" refers to the cellular processes by which a biologically active polypeptide is produced from a DNA sequence and exhibits a biological activity in a cell. As such, gene expression involves the processes of transcription and translation, but also involves post-transcriptional and post-translational processes that can influence a biological activity of a gene or gene product. These processes include, but are not limited to, RNA syntheses, processing, and transport, as well as polypeptide synthesis, transport, and post-translational modification of polypeptides.

For example, the disclosure provides methods for making an SAP polypeptide of the invention by expressing a SAP gene in a cell. In some embodiments, the cell may contain an endogenous SAP gene or fragment thereof. In other embodiments, a polynucleotide coding for an exogenous SAP polypeptide or fragment thereof may be introduced (e.g., transformed, transfected, etc.) into a cell. Suitable SAP polynucleotides that can be introduced into a cell include nucleic acid fragments as well as nucleic acid constructs or expression vectors. In preferred embodiments, the endogenous or exogenous gene encodes a human SAP polypeptide.

In some embodiments, the nucleic acid fragment, e.g., encoding a human SAP polypeptide, used to transform the host cell may include a Shine-Dalgarno site (e.g., a ribosome binding site) and a start site (e.g., the codon ATG) to initiate translation of the transcribed message to produce the enzyme. It may, also include a termination sequence to end translation. A termination sequence is typically a codon for which there exists no corresponding aminoacetyl-tRNA, thus ending polypeptide synthesis. In some embodiments, a nucleic acid construct encoding an SAP polypeptide can be delivered, for example, as an expression plasmid that, when transcribed in the cell, produces as SAP polypeptide.

In some embodiments, a suitable expression vector comprises a nucleotide sequence encoding an SAP polypeptide of the invention operably linked to at least one regulatory sequence. Regulatory sequences are art-recognized and are selected to direct expression of any of the polypeptides of the disclosure. Accordingly, the term regulatory sequence includes promoters, enhancers and other expression control elements. Exemplary regulatory sequences are described in Goeddel; *Gene Expression Technology: Methods in Enzymology*, Academic Press, San Diego, Calif. (1990). For instance, any expression control sequence that regulates the expression of a DNA sequence when operatively linked to it may be used in these vectors to express any of the polypeptides of the disclosure. Such useful expression control sequences, include, for example, the early and late promoters of SV40, tet promoter, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

In some embodiments, the nucleic acid fragment or expression system used to transform the host cell optionally may include one or more marker sequences. Generally speaking, suitable marker sequences typically encode a gene product, usually an enzyme that inactivates or otherwise detects or is detected by a compound in the growth medium. For example, the inclusion of a marker sequence may render the transformed cell resistant to an antibiotic, or it may confer compound-specific metabolism on the transformed cell. Examples of suitable marker sequences that confer resistance include kanamycin, ampicillin, chloramphenicol and tetracycline. Alternatively, rather than selective pressure, a marker gene may be used that allows for detection of particular colonies containing the gene, such as β-galactosidase, where a substrate is employed that provides for a colored product.

A variety of methods are suitable for transforming a cell of the present invention with a nucleic acid fragment or expression vector. Common transformation methods include electroporation, liposomal-mediated transformation, calcium-mediated transformation, and viral-mediated transfection In certain aspects, when a host cell is transformed with a nucleic acid fragment or expression system of the present invention, the gene (e.g., human SAP) in said system can be integrated into the chromosomal DNA of the host cells by a so-called homologous recombination and the expression system will be carried stably in the host.

In order to integrate the expression system in the vector into chromosomal DNA of the host cells, an appropriate selection marker gene may be used wherein said marker gene has a sequence homologous to the gene on chromosomal DNA of the specific host cell. Selection markers for such a purpose can be easily selected by a skilled person. As an example, a preferred marker is a gene that exists on a chromosome and relates to the metabolism of the host cells. Namely, it is preferred to use a host which has been modified in such a manner that the above-mentioned gene on the chromosome will be inactivated by an appropriate means such as a mutation. The host can then be subjected to a homologous recombination with an expression vector containing the corresponding intact gene, whereupon only transformants which contain the normal metabolism gene can grow to be selected. Therefore, if such a marker gene has been introduced to the expression vector, a homologous recombination will take place between the marker gene in said expression vector and the corresponding portion of the chromosomal DNA, whereby the expression cassette of the heterologous gene will simultaneously be integrated into the chromosomal DNA.

In some embodiments, the term "expressing" a protein in a cell also includes methods of introducing a protein itself into cells. Therefore, in certain aspects, the disclosure provides methods for making an SAP polypeptide of the invention by introducing an SAP polypeptide into a cell. Techniques for introducing polypeptides directly into a cell are known in the art and generally involve a process of cell membrane permeation. Such techniques include, but are not limited to, microinjection of SAP polypeptides; encapsulating an SAP polypeptide within membrane vesicles (e.g., liposomes, capsular bodies, erythrocyte ghosts, protoplasts, etc.) and contacting them with a cell membrane to thereby cause intracellular introduction of the SAP polypeptide by fusion; using physical methods (e.g., mechanical, chemical, electrical, etc.) that rely on macromolecules entering cells by diffusion through holes transiently introduced in their plasma membranes (e.g., scrape-loading, bead-loading, etc.); and by uptake through natural endocytosis owing to cellular phagocytosis. A method of intracellular introduction may utilize a receptor-mediated pathway, wherein one of various receptors expressed on the cell surface is set as a target and an SAP polypeptide is attached (covalently or non-covalently) to the cognate ligand that acts as a carrier moiety. Several methods have been described for introducing proteins into living cells using electrostatic adsorption, wherein the protein is first cationized and then contacted with the negatively charged surface of a cell (See Japanese Patent Publication No. 2004/049214).

In certain aspects, the disclosure provides CHO cells that express a SAP polypeptide. In some embodiments, the CHO cell expresses an exogenous SAP polypeptide. In preferred embodiments, the CHO cell expresses a human SAP polypeptide. In some embodiments, the disclosure provides CHO cells comprising a polynucleotide sequence encoding an SAP polypeptide. In preferred embodiments, the polynucleotide sequence encodes a human SAP polypeptide. Any of the aforementioned techniques may be used to "express" an SAP polypeptide of the invention in a CHO cell or any other suitable cell disclosed herein.

Where any of the glycosylation activities of the wild-type or genetically engineered cell are inducible or conditional on the presence of an inducing cue (e.g., a chemical or physical cue), the wild-type or genetically engineered cell can, optionally, be cultured in the presence of an inducing agent before, during, or subsequent to the introduction of the nucleic acid encoding a SAP polypeptide or a SAP polypeptide. For example, following introduction of the SAP polypeptide into the cell can be exposed to a chemical inducing agent that is capable of promoting the expression of one or more proteins having a wild-type or altered N-glycosylation activity. Where multiple inducing cues induce conditional expression of one or more proteins having wild-type and/or altered N-glycosylation activity, a cell can be contacted with multiple inducing agents. In some embodiments, the culture medium may be modified to produce the desired glycan structure on the SAP polypeptide. For example, the serum, glucose, and/or lipid (e.g., dolichol) concentration of the medium may be modified for optimal production of the desired SAP glycovariant. In some embodiments, the temperature, pH, and/or osmolarity of culture medium may be altered for optimal production of the desired SAP glycovariant.

A variant SAP polypeptide of the invention can be further processed in vivo or can be processed in vitro prior to or following isolation from the cell or cell medium. The further processing can include modification of one or more glycan residues of the SAP polypeptide or modification to the SAP polypeptide other than to its glycan structure(s). In some embodiments, the additional processing of the SAP polypeptide can include the addition (covalent or non-covalent joining) of one or more heterologous moieties. In some embodiments, the further processing involves enzymatic or chemical treatment of the SAP polypeptide. Enzymatic treatment can involve contacting the SAP polypeptide with one or more glycosidase, phosphodiesterase, phospholipase, glycosyltransferase, or protease for a time sufficient to induce the modification, addition, or deletion of glycan residues (e.g., galactose, mannose, fucose, sialic acid, xylose, N-acetylglucosamine, etc.) on the SAP polypeptide. Customization of an N-linked oligosaccharide chain may be accomplished by the sequential modification, addition, or deletion of the desired sugar moieties, using techniques well known in the art. Enzymatic cleavage of carbohydrate moieties on peptide variants can be achieved by the use of a variety of endo- and exo-glycosidases as described by Thotakura et al., 1987, Meth. Enzymol. 138: 350. Exemplary methods of adding sugar moieties are disclosed in U.S. Pat. Nos. 5,876,980, 6,030,815, 5,728,554, and 5,922,577.

In certain embodiments, modification of the SAP glycan structure requires the presence of one or more sugar nucleotides. Exemplary sugar nucleotides that are used in the present invention include nucleotide mono-, di- or triphosphates or analogs thereof. In a preferred embodiment, the modified sugar nucleotide is selected from a UDP-glycoside, CMP-glycoside, or a GDP-glycoside. Even more preferably, the sugar nucleotide is selected from an UDP-galactose, UDP-galactosamine, UDP-glucose, UDP-glucosamine, GDP-mannose, GDP-fucose, CMP-sialic acid, CMP-N-glycolylneuraminic acid or CMP-NeuAc. In certain embodiments, a modified sugar nucleotide is utilized to add a modified sugar residue to the SAP polypeptide. N-acetylamine derivatives of the sugar nucleotides are also of use in the method of the invention.

Chemical addition or removal of glycosyl moieties can be carried out by any suitable method. For example, chemical deglycosylation may involve exposure of the SAP polypeptide to trifluoromethanesulfonic acid, or another strong acid. This treatment results in the cleavage of most or all sugars except the linking sugar (N-acetylglucosamine or N-acetylgalactosamine), while leaving the peptide intact. Methods of chemical deglycosylation are described by Haldmuddin et al., 1987, Arch. Biochem. Biophys. 259: 52 and by Edge et al., 1981, Anal. Biochem. 118: 131. Chemical treatment can, for example, involve contacting the altered SAP polypeptide with an acid, such as hydrofluoric acid, for a time sufficient to induce modification of the SAP polypeptide. Hydrofluoric acid treatment, under certain conditions, specifically removes the mannose residues that are phosphodiester-linked to glycans, while leaving the phosphate on the glycan. An altered SAP polypeptide can be further processed by addition or removal of a phosphate group from one or more N-glycans. For example, an altered SAP polypeptide can be contacted with a mannosyl kinase or a mannosyl phosphatase.

In certain aspects, it is desirable to modify only terminal sugar moieties on the SAP polypeptide glycan structure (N-linked or O-linked oligosaccharide). In some embodiments, one or more branches of the SAP glycan structure are modified by the addition, removal, substitution or modification of at least one terminal sialic acid residue. Suitable methods for modifying glycans described herein may be used to alter only the terminal sugar moiety on the SAP glycan structure. In some embodiments, a terminal sialic acid residue having an α-2,6-linkage, α-2,8-linkage, or α-2,9-linkage is replaced with one or more terminal α-2,3-linked sialic acid residue. In a particular aspect, human SAP comprising terminal α-2,6-linked sialic residues is modified according to one of methods of the disclosure in order to replace one or more of the terminal α-2,6-linked sialic residues with one or more α-2,3-linked sialic acid residues. In some embodiments, a terminal α-2,3-linked sialic acid residue is modified to add one or more α-2,6-linked, α-2,8-linked, and/or α-2,9-linked sialic acid residues.

In certain aspects, the process of making an SAP polypeptide of the invention involves a first step of deglycosylating the SAP polypeptide. The SAP polypeptide may be partially or fully deglycosylated. In some embodiments, the first step of deglycosylation involves removing only terminal sugar moieties from at least one branch of the glycan structure on the SAP polypeptide. In some embodiments, the first step of deglycosylation removes at least one α-2,6-linked sialic acid residue. In some embodiments, the first step of deglycosylation removes at least one O-linked glycan. In some embodiments, the first step of deglycosylation removes at least one N-linked glycan. In some embodiments, the first step of deglycosylation removes all O-linked and N-linked glycans. In some embodiments, a deglycosylated SAP polypeptide (partially or fully) is further processed according to the methods of the disclosure, which includes but is not limited to, enzymatically or chemically modifying the partially or fully deglycosylated SAP polypeptide, introducing the partially or fully deglycosylated SAP polypeptide into a cell, or combination thereof, wherein the method(s) produce a variant SAP polypeptide of the invention. In some embodiments, after a partially or fully deglycosylated SAP polypeptide has been introduced into a cell, it may be further modified, in vivo or in vitro, according to the methods of the disclosure to produce a variant SAP polypeptide of the invention. Similarly, a partial or fully deglycosylated SAP polypeptide that is modified in vitro, using enzymatic or chemical methods described herein, may be introduced into a cell to produce a variant SAP polypeptide of the invention.

It is understood that an SAP polypeptide of the invention can be, but need not be, processed in a cell. For example, the disclosure also provides cell-free methods of producing a variant SAP polypeptide of the invention. In some aspects the cell-free methods include the step of contacting an SAP polypeptide, under glycosylation conditions, with a cell lysate prepared from a wild-type cell (e.g., a fungal cell, a plant cell, or an animal cell) or genetically engineered cell having at least one modified glycosylation activity, wherein contacting the SAP polypeptide with the cell lysate attaches an N-linked or O-linked oligosaccharide to the SAP polypeptide or modifies an existing N-linked or O-linked oligosaccharide on the SAP polypeptide. By "N-glycosylation conditions" is meant that a mixture (e.g., of SAP polypeptide and cell lysate) is incubated under conditions that allow for the desired altered N-glycosylation.

Suitable methods for obtaining cell lysates that preserve the activity or integrity of one or more glycosylation activities in the lysate can include the use of appropriate buffers and/or inhibitors, including nuclease, protease and phosphatase inhibitors that preserve or minimize changes in N-glycosylation activities in the cell lysate. Such inhibitors include, for example, chelators such as ethylenediaminetetraacetic acid (EDTA), ethylene glycol bis(P-aminoethyl ether) N,N,N1, N1-tetraacetic acid (EGTA), protease inhibitors such as phenylmethylsulfonyl fluoride (PMSF), aprotinin, leupeptin, antipain, and phosphatase inhibitors such as phosphate, sodium fluoride, and vanadate. Inhibitors can be chosen such that they do not interfere with or only minimally adversely affect the N-glycosylation activity, or activities, of interest. Appropriate buffers and conditions for obtaining lysates containing enzymatic activities are described in, e.g., Ausubel et al. Current Protocols in Molecular Biology (Supplement 47), John Wiley & Sons, New York (1999); Harlow and Lane, Antibodies: A Laboratory Manual Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999).

A cell lysate can be further processed to eliminate or minimize the presence of interfering substances, as appropriate. If desired, a cell lysate can be fractionated by any of a variety of methods well known to those skilled in the art, including subcellular fractionation, and chromatographic techniques such as ion exchange, hydrophobic and reverse phase, size exclusion, affinity, and hydrophobic charge-induction chromatography (see, e.g., Scopes, Protein Purification: Principles and Practice, third edition, Springer-Verlag, New York (1993); Burton and Harding, J. Chromatogr. A 814:71-81 (1998)), or any other suitable purification technique.

A cell lysate can be prepared in which whole cellular organelles remain intact and/or functional. For example, a lysate can contain one or more of intact rough endoplasmic reticulum, intact smooth endoplasmic reticulum, or intact Golgi apparatus. Suitable methods for preparing lysates containing intact cellular organelles and testing for the functionality of the organelles are described in, e.g., Moreau et al. (1991) J. Biol. Chem. 266(7):4329-4333; Moreau et al. (1991) J. Biol. Chem. 266(7):4322-4328; Rexach et al. (1991) J. Cell Biol. 114(2):219-229; and Paulik et al. (1999) Arch. Biochem. Biophys. 367(2):265-273; the disclosures of each of which are incorporated herein by reference in their entirety.

The SAP polypeptide can be contacted with just one purified protein having glycosylation activity. In some embodiments, the SAP polypeptide can be contacted with more than one purified proteins having glycosylation activity. One or more proteins having glycosylation activity can be purified using standard protein isolation techniques. An SAP polypeptide can be contacted with one or more proteins in a suitable buffer for a time sufficient to induce modification of the SAP polypeptides as described above. The SAP polypeptide can be contacted with more than one protein at the same time or sequentially. Where the SAP polypeptide is contacted sequentially to more than one protein having glycosylation activity, the SAP polypeptide can, but need not, be purified after one or more steps. That is, an SAP polypeptide can be contacted with protein activity "A" and then purified before contacting the molecule to protein activity "B". Methods of modifying peptides as such are known in the art, e.g., Lee and Park (2002) 30(6):716-720 and Fujita and Takegawa (2001) Biochem. Biophys. Res. Commun. 282(3):678-682, the disclosures of which are incorporated herein by reference in their entirety.

In certain aspects, the methods of the disclosure comprise a step of isolating an SAP polypeptide, e.g., from a cell or from components of a cell lysate. Many standard techniques for protein isolation are known in the art. For example, methods of isolating polypeptides include, but are not limited to, size-exclusion chromatography, reverse-phase chromatography, liquid chromatography (e.g., HPLC), affinity chromatography (e.g., metal chelation or immunoaffinity chromatography), ion-exchange chromatography, hydrophobic-interaction chromatography, precipitation, differential solubilization, immunoprecipitation, centrifugation (e.g., ultracentrifugation, sucrose gradient centrifugation, etc.) or any combination thereof. In some embodiments, the SAP polypeptide may be conjugated to an affinity tag to facilitate purification of the polypeptide. Suitable affinity tags for SAP purification include, but are not limited to, chitin binding protein (CBP), maltose binding protein (MBP), glutathione-S-transferase (GST), streptavidin, biotin, and poly(His) tags. Affinity tags may be produced as part of the recombinant protein (i.e., as a fusion protein comprising a heterologous affinity tag domain and an SAP polypeptide domain) or attached (covalently or non-covalently) in vivo or in vitro to the SAP polypeptide. In some embodiments, multiple steps of purification can be used to isolate an SAP polypeptide. For example, an SAP polypeptide comprising a purification tag can be affinity-purified from a cell lysate or multi-component mixture using affinity purification. Then the affinity-purified SAP polypeptide can be further purified to remove any minor unwanted contaminants by an additional purification step, e.g., size exclusion chromatography or RP-HPLC. Where a polypeptide of the invention is produced in a cell, the SAP polypeptide can be isolated from the cell itself or from the media in which cell was cultured. In some embodiments, SAP polypeptides of the invention are produced and secreted from a cell into the culture media. In these embodiments, isolation may comprise separation of the cellular fraction from the soluble, SAP-containing fraction (e.g., by centrifugation).

In some aspects, it can be advantageous to link the SAP polypeptide to a solid-phase support prior to contacting the target molecule with one or more N-glycosylation activities. Such linkage can allow for easier purification following the N-glycosylation modifications. Suitable solid-phase supports include, but are not limited to, multi-well assay plates, particles (e.g., magnetic or encoded particles), a chromatography column, or a membrane.

In some embodiments, any of the altered SAP polypeptides described herein can be attached to a heterologous moiety using enzymatic or chemical means. A "heterologous moiety" refers to any constituent that is joined (e.g., covalently or non-covalently) to the altered target molecule, which constituent is different from a constituent originally present on the SAP polypeptide. Heterologous moieties include, for example, water-soluble and -insoluble polymers, targeting moieties, therapeutic moieties, diagnostic moieties, and biomolecules.

SAP polypeptides of the invention may comprise one or more "modified" sugar residues. A modifying group can be attached to a sugar moiety by enzymatic means, chemical means or a combination thereof, thereby producing a modified sugar, e.g., modified galactose, fucose, or sialic acid. When a modified sialic acid is used, either a sialyl-transferase or a trans-sialidase can be used in these methods. The sugars may be substituted at any position that allows for the attachment of the modifying moiety, yet which still allows the sugar to function as a substrate for the enzyme used to couple the modified sugar to the peptide.

In general, the sugar moiety and the modifying group are linked together through the use of reactive groups, which are typically transformed by the linking process into a new organic functional group or unreactive species. The sugar reactive functional group(s) may be located at any position on the sugar moiety. Reactive groups and classes of reactions useful in practicing the present invention are generally those that are well known in the art of bioconjugate chemistry. Currently favored classes of reactions available with reactive sugar moieties are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, Smith and March, Advanced Organic Chemistry, 5th Ed., John Wiley & Sons, New York, 2001; Hermanson, Bioconjugate Techniques, Academic Press, San Diego, 1996; and Feeney et al., Modification of Proteins; Advances in Chemistry Series, Vol. 198, American Chemical Society, Washington, D.C., 1982.

Useful reactive functional groups pendent from a sugar nucleus or modifying group include, but are not limited to: (a) carboxyl groups and various derivatives thereof (e.g., N-hydroxysuccinimide esters, N-hydroxybenzotriazole esters, acid halides, acyl imidazoles, thioesters, p-nitrophenyl esters, alkyl, alkenyl, alkynyl and aromatic esters); (b) hydroxyl groups, which can be converted to, e.g., esters, ethers, aldehydes, etc.; (c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom; (d) dienophile groups, which are capable of participating in Diels-Alder reactions such as, for example, maleimido groups (e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (e) thiol groups, which can be, for example, converted to disulfides or reacted with alkyl and acyl halides; (h) amine or sulfhydryl groups, which can be, for example, acylated, alkylated or oxidized; (i) alkenes, which can undergo, for example, cycloadditions, acylation, Michael addition, metathesis, Heck reaction, etc.; (j) epoxides, which can react with, for example, amines and hydroxyl compounds.

The reactive functional groups can be chosen such that they do not participate in, or interfere with, the reactions necessary to assemble the reactive sugar nucleus or modifying group. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., Protective Groups in Organic Synthesis, John Wiley & Sons, New York, 1991.

In some embodiments, the modified sugar is an activated sugar. Activated modified sugars useful in the present invention are typically glycosides which have been synthetically altered to include an activated leaving group. As used herein, the term "activated leaving group" refers to those moieties which are easily displaced in enzyme-regulated nucleophilic substitution reactions. Many activated sugars are known in the art. See, for example, Vocadlo et al., In Carbohydrate Chemistry and Biology, Vol. 2, Ernst et al. Ed., Wiley-VCH Verlag: Weinheim, Germany, 2000; Kodama et al., Tetrahedron Lett. 34: 6419 (1993); Lougheed, et al., J. Biol. Chem. 274: 37717 (1999)). Examples of such leaving groups include fluoro, chloro, bromo, tosylate, mesylate, triflate and the like. Preferred activated leaving groups for use in the present invention are those that do not significantly sterically encumber the enzymatic transfer of the glycoside to the acceptor. Accordingly, preferred embodiments of activated glycoside derivatives include glycosyl fluorides and glycosyl mesylates, with glycosyl fluorides being particularly preferred. Among the glycosyl fluorides, $\alpha$-galactosyl fluoride, $\alpha$-mannosyl fluoride, $\alpha$-glucosyl fluoride, $\alpha$-fucosyl fluoride, $\alpha$-xylosyl fluoride, $\alpha$-sialyl fluoride, $\alpha$-N-acetylglucosaminyl fluoride, $\alpha$-N-acetylglucosaminyl fluoride, $\beta$-galactosyl fluoride, $\beta$-mannosyl fluoride, .beta.-glucosyl fluoride, $\beta$-fucosyl fluoride, $\beta$-xylosyl fluoride, $\beta$-sialyl fluoride, $\beta$-N-acetylglucosaminyl fluoride and $\beta$-N-acetylgalactosaminyl fluoride are most preferred.

In certain aspects, a modified sugar residue is conjugated to one or more water-soluble polymers. Many water-soluble polymers are known to those of skill in the art and are useful in practicing the present invention. The term water-soluble polymer encompasses species such as saccharides (e.g., dextran, amylose, hyaluronic acid, poly(sialic acid), heparans, heparins, etc.); poly(amino acids); nucleic acids; synthetic polymers (e.g., poly(acrylic acid), poly(ethers), e.g., poly (ethylene glycol)); peptides, proteins, and the like. The present invention may be practiced with any water-soluble polymer with the sole limitation that the polymer must include a point at which the remainder of the conjugate can be attached.

Methods and chemistry for activation of water-soluble polymers and saccharides as well as methods for conjugating saccharides and polymers to various species are described in the literature. Commonly used methods for activation of polymers include activation of functional groups with cyanogen bromide, periodate, glutaraldehyde, bi-epoxides, epichlorohydrin, divinyl sulfone, carbodiimide, sulfonyl halides, trichlorotriazine, etc. (see, R. F. Taylor, (1991), Protein Immobilization, Fundamentals and Applications, Marcel Dekker, N.Y.; S. S. Wong, (1992), Chemistry of Protein Conjugation and Crosslinking, CRC Press, Boca Raton; G. T. Hermanson et al., (1993), Immobilized Affinity Ligand Techniques, Academic Press, N.Y.; Dunn, R. L., et al., Eds. Polymeric Drugs and Drug Delivery Systems, ACS Symposium Series Vol. 469, American Chemical Society, Washington, D.C. 1991).

In certain aspects, a modified sugar residue is conjugated to one or more water-insoluble polymers. In some embodiments, conjugation to a water-insoluble polymer can be used to deliver a therapeutic peptide in a controlled manner. Polymeric drug delivery systems are known in the art. See, for example, Dunn et al., Eds. Polymeric drugs and Drug Delivery Systems, ACS Symposium Series Vol. 469, American Chemical Society, Washington, D.C. 1991. Those of skill in the art will appreciate that substantially any known drug delivery system is applicable to the conjugates of the present invention.

Representative water-insoluble polymers include, but are not limited to, polyphosphazenes, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly(ethylene glycol), poly(ethylene oxide), poly(ethylene terephthalate), poly(vinyl acetate), polyvinyl chloride, polystyrene, polyvinyl pyrrolidone, pluronics, and polyvinylphenol, and copolymers thereof.

These and the other polymers discussed herein can be readily obtained from commercial sources such as Sigma Chemical Co. (St. Louis, Mo.), Polysciences (Warrenton, Pa.), Aldrich (Milwaukee, Wis.), Fluka (Ronkonkoma, N.Y.), and BioRad (Richmond, Calif.), or else synthesized from monomers obtained from these suppliers using standard techniques. Representative biodegradable polymers useful in the conjugates of the invention include, but are not limited to, polylactides, polyglycolides and copolymers thereof poly(ethylene terephthalate), poly(butyric acid), poly(valeric acid), poly(lactide-co-caprolactone), poly(lactide-co-glycolide), polyanhydrides, polyorthoesters, blends and copolymers thereof. Of particular use are compositions that form gels, such as those including collagen, and pluronics.

In a preferred embodiment, one or more modified sugar residues are conjugated to one or more PEG molecules.

In certain aspects, the modified sugar is conjugated to a biomolecule. Biomolecule of the invention may include, but are not limited to, functional proteins, enzymes, antigens, antibodies, peptides, nucleic acids (e.g., single nucleotides or nucleosides, oligonucleotides, polynucleotides and single- and higher-stranded nucleic acids), lectins, receptors or a combination thereof. Some preferred biomolecules are essentially non-fluorescent, or emit such a minimal amount of fluorescence that they are inappropriate for use as a fluorescent marker in an assay. Other biomolecules may be fluorescent.

In some embodiments, the biomolecule is a targeting moiety. A "targeting moiety" and "targeting agent", as used herein, refer to species that will selectively localize in a particular tissue or region of the body. In some embodiments, a biomolecule is selected to direct the SAP polypeptide of the invention to a specific intracellular compartment, thereby enhancing the delivery of the peptide to that intracellular compartment relative to the amount of underivatized peptide that is delivered to the tissue. The localization is mediated by specific recognition of molecular determinants, molecular size of the targeting agent or conjugate, ionic interactions, hydrophobic interactions and the like. Other mechanisms of targeting an agent to a particular tissue or region are known to those of still in the art.

In some embodiments, the modified sugar includes a therapeutic moiety. Those of skill in the art will appreciate that there is overlap between the category of therapeutic moieties and biomolecules, i.e., many biomolecules have therapeutic properties or potential.

Classes of useful therapeutic moieties include, for example, non-steroidal anti-inflammatory drugs; steroidal anti-inflammatory drugs; adjuvants; antihistaminic drugs; antitussive drugs; antipruritic drugs; anticholinergic drugs; anti-emetic and antinauseant drugs; anorexic drugs; central stimulant drugs; antiarrhythmic drugs; β-adrenergic blocker drugs; cardiotonic drugs; antihypertensive drugs; diuretic drugs; vasodilator drugs; vasoconstrictor drugs; antiulcer drugs; anesthetic drugs; antidepressant drugs; tranquilizer and sedative drugs; antipsychotic drugs; and antimicrobial drugs.

Other drug moieties useful in practicing the present invention include antineoplastic drugs, cytocidal agents, anti-estrogens, and antimetabolites. Also included within this class are radioisotope-based agents for both diagnosis (e.g., imaging) and therapy, and conjugated toxins.

The therapeutic moiety can also be a hormone, a muscle relaxant, an antispasmodic, bone activating agent, endocrine modulating agent, modulator of diabetes, androgen, antidiuretics, or calcitonin drug.

Other useful modifying groups include immunomodulating drugs, immunosuppressants, etc. Groups with anti-inflammatory activity, such as sulindac, etodolac, ketoprofen and ketorolac, are also of use. Other drugs of use in conjunction with the present invention will be apparent to those of skill in the art.

The altered N-glycosylation SAP polypeptides produced by the methods of the disclosure can be homogeneous (i.e., the sample of SAP polypeptide is uniform in specific N-glycan structure) or substantially homogeneous. By "substantially homogeneous" is meant that at least about 25% (e.g., at least about 27%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, or at least about 99%) of the SAP polypeptides contain the same specific N-glycan structure.

In some embodiments, variant SAP polypeptides of the invention have an $IC_{50}$ for inhibiting the differentiation of monocytes into fibrocytes in vitro that is less than ½, less than ⅓, less than ¼, less than 1/10, or less than 1/100 that of a corresponding sample of wild-type SAP isolated from human serum. There are many well characterized methods for determining the responsiveness of Peripheral Blood Mononuclear Cells (PBMCs) or monocyte cells to SAP for fibrocyte differentiation. These methods may be used to determine the relative potency of any of the SAP variant polypeptides of the invention in comparison to a sample of human serum-derived SAP, any other SAP variant polypeptide, or other fibrocyte suppressant or activating agent. PBMCs or monocytes suitable for use in these methods may be obtained from various tissue culture lines. Alternatively, suitable cells for fibrocyte differentiation assays may be obtained from any biological sample that contains PBMC or monocyte cells. The biological sample may be obtained from serum, plasma, healthy tissue, or fibrotic tissue. In general, fibrocyte differentiation assays are conducted by incubating PBMC or monocyte cells in media with various concentrations of a SAP polypeptide to determine the degree of fibrocyte differentiation. The concentration of SAP can range from 0.0001 µg/mL to 1 mg/ml, and in some embodiments is 0.001 µg/mL, 1.0 µg/mL, 5 µg/mL, 10 µg/mL, 15 µg/mL, 20 µg/mL, 25 µg/mL, 30 µg/mL, 35 µg/mL, 40 µg/mL, 45 µg/mL, 50 µg/mL, 100 µg/mL, 200 µg/mL, 300 µg/mL, or 500 µg/mL In some assays, the media can be supplemented with between 1-100 ng/ml hMCSF; the preferred concentration of hMCSF being 25 ng/mL The indication that PBMC and monocytes have differentiated into fibrocytes can be determined by one skilled in the art. In general, fibrocytes are morphologically defined as adherent cells with an elongated spindle-shape and the presence of an oval nucleus. In some assays, cells are fixed and stained with Hema 3 before enumerating fibrocytes by direct counting, e.g., using an inverted microscope. The amount of fibrocyte differentiation is interpreted by one skilled in the art as an indication of a cell's responsiveness to SAP. As indicated by the examples of the disclosure, a greater suppression of fibrocyte differentiation indicates a greater degree of SAP responsiveness. An alternative method of measuring fibrocyte differentiation involves determining the expression of fibrocyte-specific cell surface markers or secreted factors, e.g., cytokines (e.g., IL-1ra, ENA-78/CXCL-5, PAI-1), fibronectin, collagen-1. Methods of detecting and/or quantifying cell surface markers or secreted factors are well known in the art, including but not limited to various ELISA- and FACS-based techniques using immunoreactive antibodies against one or more fibrocyte specific markers. As described in the examples of the disclosure, measuring the expression of Macrophage Derived Chemokine (MDC) is an effective method of determining fibrocyte differentiation.

Methods for detecting and/or characterizing N-glycosylation (e.g., altered N-glycosylation) of a SAP polypeptide include DNA sequencer-assisted (DSA), fluorophore-assisted carbohydrate electrophoresis (FACE) or surface-enhanced laser desorption/ionization time-of-flight mass spectrometry (SELDI-TOF MS). For example, an analysis can utilize DSA-FACE in which, for example, glycoproteins are denatured followed by immobilization on, e.g., a membrane. The glycoproteins can then be reduced with a suitable reducing agent such as dithiothreitol (DATA) or β-mercaptoethanol. The sulfhydryl groups of the proteins can be carboxylated using an acid such as iodoacetic acid. Next, the N-glycans can be released from the protein using an enzyme such as N-glycosidase F. N-glycans, optionally, can be reconstituted and derivatized by reductive amination. The derivatized N-glycans can then be concentrated. Instrumentation suitable for N-glycan analysis includes, for example, the ABI PRISM® 377 DNA sequencer (Applied Biosystems). Data analysis can be performed using, for example, GENES-CAN®. 3.1 software (Applied Biosystems). Optionally, isolated mannoproteins can be further treated with one or more enzymes to confirm their N-glycan status. Exemplary enzymes include, for example, α-mannosidase or α-1,2 mannosidase. Additional methods of N-glycan analysis include, for example, mass spectrometry (e.g., MALDI-TOF-MS), high-pressure liquid chromatography (HPLC) on normal phase, reversed phase and ion exchange chromatography (e.g., with pulsed amperometric detection when glycans are not labeled and with UV absorbance or fluorescence if glycans are appropriately labeled). See also Callewaert et al. (2001) Glycobiology 11(4):275-281 and Freire et al. (2006) Bioconjug. Chem. 17(2):559-564, the disclosures of each of which are incorporated herein by reference in their entirety Treatment Methods In one aspect, the disclosure provides methods for treating an SAP-responsive disorder in a patient by administering a therapeutically effective amount of a variant SAP polypeptide of the invention to a patient in need thereof. The dosage and frequency of treatment can be determined by one skilled in the art and will vary depending on the symptoms, age and body weight of the patient, and the nature and severity of the disorder to be treated or prevented. In some embodiments, a variant SAP polypeptide is administered to a patient once or twice per day, once or twice per week, once or twice per month, or just prior to or at the onset of symptoms.

Dosages may be readily determined by techniques known to those of skill in the art or as taught herein. Toxicity and therapeutic efficacy of SAP may be determined by standard pharmaceutical procedures in experimental animals, for example, determining the $LD_{50}$ and the $ED_{50}$. The $ED_{50}$ (Effective Dose 50) is the amount of drug required to produce a specified effect in 50% of an animal population. The $LD_{50}$ (Lethal Dose 50) is the dose of drug which kills 50% of a sample population.

In some embodiments, the SAP-responsive disorder is fibrosis. The use of SAP as a therapeutic treatment for fibrosis is described in U.S. Patent Application No. 2007/0243163, which is hereby incorporated by reference. Fibrosis related disorders that may be amenable to treatment with the subject method include, but are not limited to, collagen disease, interstitial lung disease, human fibrotic lung disease (e.g., obliterative bronchiolitis, idiopathic pulmonary fibrosis, pulmonary fibrosis from a known etiology, tumor stroma in lung disease, systemic sclerosis affecting the lungs, Hermansky-Pudlak syndrome, coal worker's pneumoconiosis, asbestosis, silicosis, chronic pulmonary hypertension, AIDS-associated pulmonary hypertension, sarcoidosis, moderate to severe asthma and the like), fibrotic vascular disease, arterial sclerosis, atherosclerosis, varicose veins, coronary infarcts, cerebral infarcts, myocardial fibrosis, musculoskeletal fibrosis, post-surgical adhesions, human kidney disease (e.g., nephritic syndrome, Alport syndrome, HIV-associated nephropathy, polycystic kidney disease, Fabry's disease, diabetic nephropathy, chronic glomerulonephritis, nephritis associated with systemic lupus, and the like), progressive systemic sclerosis (PSS), primary scalloping cholangitis (PSC), liver fibrosis, liver cirrhosis, renal fibrosis, pulmonary fibrosis, cystic fibrosis, chronic graft versus host disease, scleroderma (local and systemic), Grave's opthalmopathy, diabetic retinopathy, glaucoma, Peyronie's disease, penis fibrosis, urethrostenosis after cystoscope, inner accretion after surgery, scarring, myelofibrosis, idiopathic retroperitoneal fibrosis, peritoneal fibrosis from a known etiology, drug-induced ergotism, fibrosis incident to benign or malignant cancer, fibrosis incident to microbial infection (e.g., viral, bacterial, parasitic, fungal, etc.), Alzheimer's disease, fibrosis incident to inflammatory bowel disease (including stricture formation in Crohn's disease and microscopic colitis), stromal cell tumors, mucositis, fibrosis induced by chemical or environmental insult (e.g., cancer chemotherapy, pesticides, or radiation (e.g., cancer radiotherapy)).

In some embodiments, the fibrosis related disorder is selected from systemic or local scleroderma, keloids, hypertrophic scars, atherosclerosis, restenosis, pulmonary inflammation and fibrosis, idiopathic pulmonary fibrosis, liver cirrhosis, fibrosis as a result of chronic hepatitis B or C infection, kidney disease, heart disease resulting from scar tissue, macular degeneration, and retinal and vitreal retinopathy. In some embodiments, the fibrosis related disorder results from chemotherapeutic drugs, radiation-induced fibrosis, and injuries and burns. In some embodiments, the fibrosis-related disorder or condition results from post-surgical scarring, e.g., following trabeculectomy or other filtration surgery of the eye.

In some embodiments, the SAP-responsive disorder is a hypersensitivity disorder such as those mediated by Th1 or Th2 responses. The use of SAP as a therapeutic treatment for hypersensitivity disorders is also described in U.S. Provisional Application No. 61/209,795, which is hereby incorporated by reference. Hypersensitivity related disorders that may be amenable to treatment with SAP include, but are not limited to, allergic rhinitis, allergic sinusitis, allergic conjunctivitis, allergic bronchoconstriction, allergic dyspnea, allergic increase in mucus production in the lungs, atopic eczema, dermatitis, urticaria, anaphylaxis, pneumonitis, and allergic-asthma.

In some embodiments, a variant SAP polypeptide of the invention may be used to treat allergen-specific immune responses, such as anaphylaxis, to various antigens, including, but not limited to, antimicrobials (e.g., cephalosporins, sulfonamides, penicillin and other β-lactams), anticonvulsants (e.g., phenyloin, phenobarbital, carbamazepine, dapsone, allopurinol, and minocycline), chemotherapeutics (e.g., taxanes, platinum compounds, asparaginases, and epipodophyllotoxins), heparin, insulin, protamine, aspirin and other non-steroidal anti-inflammatory drugs, muscle relaxants (e.g., succinylcholine, atracurium, vecuronium, and pancuronium), induction agents (e.g., barbiturates, etomidate, propofol), narcotics (e.g., fentanyl, meperidine, morphine), colloids for intravascular volume expansion, radiocontrast materials, blood products, latex, animal products, animal dander, dust mites, insects (e.g., bites, stings or venom), cosmetics, metals (e.g., nickel, cobalt, and chromate), plants, spores, pollen, food (e.g., milk, eggs, wheat, soy, peanuts and tree nuts, seafood), vaccination, and fungal antigens (e.g., *Aspergillus, Curvularia, Exserohilum*, and *Alternaria* species).

In some embodiments, the SAP-responsive disorder is an autoimmune disorder such as those mediated by Th1 or Th2 responses. The use of SAP as a therapeutic treatment for autoimmune disorders is also described in U.S. Provisional Application No. 61/209,845, which is hereby incorporated by reference. Autoimmune related disorders that may be amenable to treatment with SAP include, but are not limited to, type I diabetes, multiple sclerosis, rheumatoid arthritis, psoriatic arthritis, autoimmune myocarditis, pemphigus, myasthenia gravis, Hashimoto's thyroiditis, Graves' disease, Addison's disease, autoimmune hepatitis, chronic Lyme arthritis, familial dilated cardiomyopathy, juvenile dermatomyositis, polychondritis, Sjogren's syndrome, psoriasis, juvenile idiopathic arthritis, inflammatory bowel disease, systemic lupus erythematosus, chronic obstructive pulmonary disease, and graft-versus-host disease.

In some embodiments, the SAP-responsive disorder is a mucositis. The use of SAP as a therapeutic treatment for mucositis is also described in U.S. application Ser. No. 12/217,614, which is hereby incorporated by reference. Methods of the invention may be useful for treating oral, esophageal, and gastrointestinal mucositis, as well as gastric and duodenal ulcers, or erosions of the stomach and esophagus.

In some embodiments, a variant SAP polypeptide of the invention may be used to treat an inflammatory disease or condition. In some embodiments, the inflammatory disease may be a viral, bacterial, fungal, or parasitic infection. The use of SAP as a therapeutic treatment for viral infection has also been described in U.S. Pat. No. 6,406,698 and in International Patent Application No. WO1997/026906, which are both incorporated by reference herein.

Pharmaceutical Preparations and Formulations

In certain embodiments, the methods described herein involve administration of at least one variant SAP polypeptide of the invention to a subject as a therapeutic agent. The therapeutic agents of the invention may be formulated in a conventional manner using one or more physiologically acceptable carriers or excipients. For example, therapeutic agents and their physiologically acceptable salts and solvates may be formulated for administration by, for example, injection (e.g. SubQ, IM, IP), inhalation or insufflation (either through the mouth or the nose) or oral, buccal, sublingual, transdermal, nasal, parenteral or rectal administration. In certain embodiments, therapeutic agents may be administered locally, at the site where the target cells are present, i.e., in a specific tissue, organ, or fluid (e.g., blood, cerebrospinal fluid, tumor mass, etc.).

The present invention further provides use of any variant SAP polypeptide of the invention in the manufacture of a medicament for the treatment or prevention of a disorder or a condition, as described herein, in a patient, for example, the use of a variant SAP polypeptide in the manufacture of medicament for the treatment of a disorder or condition described herein. In some aspects, any variant SAP polypeptide of the invention may be used to make a pharmaceutical preparation for the use in treating or preventing a disease or condition described herein.

Therapeutic agents can be formulated for a variety of modes of administration, including systemic and topical or localized administration. Techniques and formulations generally may be found in Remington's Pharmaceutical Sciences, Meade Publishing Co., Easton, Pa. For parenteral administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and dissolved or suspended immediately prior to use. Lyophilized forms are also included. In some embodiments, the therapeutic agents can be administered to cells by a variety of methods know to those familiar in the art, including, but not restricted to, encapsulation in liposomes, by iontophoresis, or by incorporation into other vehicles, such as hydrogels, cyclodextrins, biodegradable nanocapsules, and bioadhesive micro spheres.

For oral administration, the pharmaceutical compositions may take the form of, for example, tablets, lozenges, or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation (e.g., pulmonary delivery), therapeutic agents may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin, for use in an inhaler or insufflator may be formulated containing a powder mix of the compound and a suitable powder base such as lactose or starch.

In the methods of the invention, the pharmaceutical compounds can also be administered by intranasal or intrabronchial routes including insufflation, powders, and aerosol formulations (for examples of steroid inhalants, see Rohatagi (1995) J. Clin. Pharmacology. 35:1187-1193; Tjwa (1995) Ann Allergy Asthma Immunol. 75:107-111). For example, aerosol formulations can be placed into pressurized acceptable propellants, such as dichlorodifluoromethane, propane, nitrogen, and the like. They also may be formulated as pharmaceuticals for non-pressured preparations such as in a nebulizer or an atomizer. Typically, such administration is in an aqueous pharmacologically acceptable buffer.

Pharmaceutical compositions suitable for respiratory delivery (e.g., intranasal, inhalation, etc.) of variant SAP polypeptides may be prepared in either solid or liquid form.

SAP polypeptides of the invention may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In addition, SAP polypeptides of the invention may also be formulated as a depot preparation. Such long-acting formulations may be administered by implantation (for example subcutaneously or intramuscularly) or by intramuscular injection. Thus, for example, therapeutic agents may be formulated with suitable polymeric or hydrophobic materials (for example as an emulsion in an acceptable oil) or ion exchange resins, or as sparingly soluble derivatives, for example, as a sparingly soluble salt. Controlled release formula also includes patches.

In certain embodiments, the compounds described herein can be formulated for delivery to the central nervous system (CNS) (reviewed in Begley, Pharmacology & Therapeutics 104: 29-45 (2004)). Conventional approaches for drug delivery to the CNS include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the blood-brain-barrier in an attempt to exploit one of the endogenous transport pathways of the blood-brain-barrier); pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

In certain embodiments, SAP polypeptides of the invention are incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Pharmaceutical compositions (including cosmetic preparations) may comprise from about 0.00001 to 100% such as from 0.001 to 10% or from 0.1% to 5% by weight of one or more of the variant SAP polypeptides described herein. In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Conditions of the eye can be treated or prevented by, e.g., systemic, topical, intraocular injection of therapeutic agents, or by insertion of a sustained release device that releases therapeutic agents. SAP polypeptides of the invention may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, conjunctiva, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material. Alternatively, the compounds may be injected directly into the vitreous and aqueous humour. In a further alternative, the compounds may be administered systemically, such as by intravenous infusion or injection, for treatment of the eye.

Therapeutic agents described herein may be stored in oxygen-free environment according to methods in the art.

Exemplary compositions comprise an SAP polypeptide with one or more pharmaceutically acceptable carriers and, optionally, other therapeutic ingredients. The carrier(s) must be "pharmaceutically acceptable" in the sense of being compatible with the other ingredients of the composition and not eliciting an unacceptable deleterious effect in the subject. Such carriers are described herein or are otherwise well known to those skilled in the art of pharmacology. In some embodiments, the pharmaceutical compositions are pyrogen-free and are suitable for administration to a human patient. In some embodiments, the pharmaceutical compositions are irritant-free and are suitable for administration to a human patient. In some embodiments, the pharmaceutical compositions are allergen-free and are suitable for administration to a human patient. The compositions may be prepared by any of the methods well known in the art of pharmacy.

In some embodiments, an SAP polypeptide is administered in a time release formulation, for example in a composition which includes a slow release polymer. An SAP polypeptide can be prepared with carriers that will protect against rapid release. Examples include a controlled release vehicle, such as a polymer, microencapsulated delivery system, or bioadhesive gel. Alternatively, prolonged delivery of an SAP polypeptide may be achieved by including in the composition agents that delay absorption, for example, aluminum monostearate hydrogels and gelatin.

Methods for delivering nucleic acid compounds are known in the art (see, e.g., Akhtar et al., 1992, Trends Cell Bio., 2, 139; and Delivery Strategies for Antisense Oligonucleotide Therapeutics, ed. Akhtar, 1995; Sullivan et al., International Application No. WO 94/02595). These protocols can be utilized for the delivery of virtually any nucleic acid compound. Nucleic acid compounds can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to, oral (tablet or pill form) and/or intrathecal delivery (Gold, 1997, Neuroscience, 76, 1153-1158). Other approaches include the use of various transport and carrier systems, for example though the use of conjugates and biodegradable polymers. For a comprehensive review on drug delivery strategies, see Ho et al., 1999, Curr. Opin. Mol. Ther., 1, 336-343 and Jain, Drug Delivery Systems: Technologies and Commercial Opportunities, Decision Resources, 1998 and Groothuis et al., 1997, J. Neuro Virol., 3, 387-400. More detailed descriptions of nucleic acid delivery and administration are provided in Sullivan et al., supra, Draper et al., PCT WO93/23569, Beigelman et al., International Application No. WO99/05094, and Klimuk et al., International Publication No. WO99/04819.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXEMPLIFICATION

Example 1

Recombinant SAP is More Potent than Human Serum-Derived SAP

Recombinant human SAP isolated from CHO—S cells (rhSAP) and human serum-derived SAP (hSAP) were assayed for bioactivity using an in vitro bioassay. In this assay, monocyte enriched Peripheral Blood Mononuclear Cells (PBMCs) were incubated with varying concentrations of either rhSAP or hSAP for 96 hours. Following this incubation, resulting culture supernatants were removed and assayed by ELISA to quantify the amount of Macrophage Derived Chemokine (MDC) that was produced. MDC is produced by fibrocytes and therefore an indicator of monocyte differentiation into fibrocytes. By comparing the inhibitory concentration, 50% ($IC_{50}$) of the sample to the hSAP reference standard, the relative potency of a SAP glycovariant can be determined. The result is expressed as an $IC_{50}$ ratio of the sample versus the hSAP reference standard.

All SAP samples and standards were initially diluted to a concentration of 1.0 mg/mL in Supplemented FibroLife Media. SAP standards were serially diluted to generate working standard concentrations of 60, 30, 20, 13.4, 8.8, 6.0, 3.0, 1.5, and 0.75 µg/mL (final standard concentration of 30, 15, 10, 6.7, 4.4, 3.0. 1.5, 0.75, and 0.375 µg/mL) See the following Table 1.

| Working rhSAP Standard Concentration (µg/mL) | Volume of Standard | Volume of Supplemented FibroLife Media |
|---|---|---|
| 60 | 60 (1 mg/mL) | 940 |
| 30 | 600 (60 µg/mL) | 600 |
| 20 | 800 (30 µg/mL Std) | 400 |
| 13.4 | 800 (20 µg/mL Std) | 400 |
| 8.8 | 800 (13.4 µg/mL Std) | 400 |
| 6.0 | 800 (8.8 µg/mL Std) | 400 |
| 3.0 | 600 (6.0 µg/mL Std) | 600 |
| 1.5 | 600 (3.0 µg/mL Std) | 600 |
| 0.75 | 600 (1.5 µg/mL Std) | 600 |

To prepare for the ELISA assay, the capture antibody (i.e., mouse anti-human MDC) was diluted to the working concentration in PBS without carrier protein. The diluted capture antibody was used to coat 96-well plates, and then each plate was sealed and incubated overnight at room temperature. Before using the coated plates, each well was aspirated and washed with wash buffer, repeating the process two times for a total of three washes. The plates were then blocked by adding 300 µL of reagent diluent to each well and incubating at room temperature for one hour. After incubation the aspiration and well-washing procedure was repeated.

For the ELISA assay, 100 µL samples of either the supernatants from the monocyte/fibrocyte cultures or the SAP standards were added to each well. The plate was then incubated at room temperature for 2 hours before aspirating and washing the wells. Then 100 µL of a working dilution of Streptavidin-HRP was added to each well. The plate was incubated for 20 minutes at room temperature before adding 50 µL of Stop Solution to each well. Immediately, the optical density of each well was measured using a microplate reader set to 450 nm. If wavelength correction was available, the microplate reader was set to 540 nm or 570 nm. If wavelength correction was not available, then the readings at 540 nm or 570 nm were subtracted from the readings at 450 nm. This subtraction corrects for optical imperfections in the plate.

Both RHSAP and hSAP were assayed for bioactivity using this assay (FIG. 1). On average, RHSAP is 3.4-fold more active than hSAP (average of 7 independent experiments).

Example 2

Modification of SAP Glycan Structures

Using in vitro glycoremodeling techniques, glycan moieties on a sample of recombinant human SAP (rhSAP) were modified to replace terminal α-2,3-linked sialic acid moieties with α-2,6-linked sialic acid moieties (FIGS. 2, A and B). Similarly, a sample of human serum-derived SAP (hSAP) was also modified to replace terminal α-2,6-linked sialic acid moieties with α-2,3-linked sialic acid moieties (FIGS. 2, C and D). In addition, as rhSAP isolated from CHO—S cells is only partially sialylated, a sample of rhSAP was treated to fully sialylate the attached glycan structures with α-2,3-linked sialic acid moieties (FIGS. 2, E and F).

Both rhSAP and hSAP (Calbiochem Cat#970549) were treated with a α-2,3,6,8,9-sialidase (Sigma Cat #N8271) to fully desialylate the polypeptides. After sialidase treatment for 17 hours, desialylated (i.e. asialo) rhSAP and hSAP were purified using phosphoethanolamine (PE) affinity and size exclusion (Sephadex 200 prep grade) chromatography. Purified asialo SAP polypeptides were then enzymatically treated using either α-2,3- or α-2,6-sialyltransferases (Calbiochem Cat #566223) in the presence of CMP-sialic acid (Calbiochem Cat #233264) for 17 hours at 37° C. The following tables provide details on each reaction mixture.

| | Asialo rhSAP Reactions (Rxns) | | |
|---|---|---|---|
| | parameter | units | value |
| Treatment with α2,3 sialyltransferase (ST3Gal3) | | | |
| rhSAP, ST3Gal3 reagent stocks | [asialo rhSAP] stk | mg/mL | 10.8 |
| | asialo rhSAP MW | g/mol | 116293 |
| | [asialo rhSAP] stk | μM | 93 |
| | max [Galactose] | μM | 929 |
| | [ST3Gal3] stk | mg/mL | 0.9 |
| | ST3Gal3 MW | g/mol | 84000 |
| | [ST3Gal3] stk | μM | 10.7 |
| | [CMP-SA] stk | mg/mL | 25 |
| | CMP-SA MW | g/mol | 658.4 |
| | [CMP-SA] stk | mM | 38 |
| rxn volumes | μL asialo rhSAP in rxn | μL | 260 |
| | μL ST3Gal3 in rxn | μL | 50 |
| | μL CMP-SA in rxn | μL | 75 |
| | buffer (10 mM HEPES/150 mM NaCl, pH 8) | μL | 615 |
| | tot rxn vol | μL | 1000 |
| rxn concentrations | [asialo rhSAP] rxn | μM | 24.1 |
| | max [Galactose] | μM | 241 |
| | [SAP] rxn | mg/mL | 2.8 |
| | [ST3Gal3] rxn | μM | 0.5357 |
| | [ST3Gal3] rxn | mg/mL | 0.045 |
| | [CMP-SA] rxn | mM | 2.85 |
| | asialo rhSAP:ST3 | mass ratio | 62 |
| | asialo rhSAP:ST3 | molar ratio | 45 |
| | CMP-SA:ST3 | molar ratio | 5316 |
| | CMP-SA:asialo rhSAP | molar ratio | 118 |
| | CMP-SA:Galactose | molar ratio | 11.8 |
| Treatment with α2,6 sialyltransferase (ST6 Rxn) | | | |
| rhSAP, ST6 reagent stocks | [asialo rhSAP] stk | mg/mL | 10.8 |
| | asialo rhSAP MW | g/mol | 116293 |
| | [asialo rhSAP] stk | μM | 93 |
| | max [Galactose] | μM | 929 |
| | [ST6] stk | mg/mL | 0.205 |
| | ST6 MW | g/mol | 42000 |
| | [ST6] stk | μM | 4.9 |
| | [CMP-SA] stk | mg/mL | 25 |
| | CMP-SA MW | g/mol | 658.4 |
| | [CMP-SA] stk | mM | 38 |
| rxn volumes | μL asialo rhSAP 1 in rxn | μL | 260 |
| | μL ST6 in rxn | μL | 30 |
| | μL CMP-SA in rxn | μL | 75 |
| | buffer (10 mM HEPES/150 mM NaCl, pH 8) | μL | 635 |
| | tot rxn vol | μL | 1000 |
| rxn concentrations | [asialo rhSAP] rxn | μM | 24.1 |
| | max [Galactose] | μM | 241 |
| | [asialo rhSAP] rxn | mg/mL | 2.8 |
| | [ST6] rxn | μM | 0.146 |
| | [ST6] rxn | mg/mL | 0.006 |
| | [CMP-SA] rxn | mM | 2.85 |
| | asialo rhSAP:ST6 | mass ratio | 457 |
| | asialo rhSAP:ST6 | molar ratio | 165 |
| | CMP-SA:ST6 | molar ratio | 19448 |
| | CMP-SA:asialo rhSAP | molar ratio | 118 |
| | CMP-SA:Galactose | molar ratio | 11.8 |

| | Asialo hSAP Rxns | | |
|---|---|---|---|
| | parameter | units | value |
| Treatment with α2,3 sialyltransferase (ST3Gal3) | | | |
| hSAP, ST3Gal3 reagent stocks | [asialo hSAP] stk | mg/ml | 5.6 |
| | SAP MW | g/mol | 116293 |
| | [asialo hSAP] stk | μM | 48 |
| | max [Galactose] | μM | 482 |
| | [ST3Gal3] stk | mg/mL | 0.9 |
| | ST3Gal3 MW | g/mol | 84000 |
| | [ST3Gal3]stk | μM | 10.7 |
| | [CMP-SA] stk | mg/mL | 25 |
| | CMP-SA MW | g/mol | 658.4 |
| | [CMP-SA] stk | mM | 38 |
| rxn volumes | μL asialo hSAP in rxn | μL | 500 |
| | μL ST3Gal3 in rxn | μL | 50 |
| | μL CMP-SA in rxn | μL | 75 |
| | buffer (10 mM HEPES/150 mM NaCl, pH 8) | μL | 375 |
| | tot rxn vol | μL | 1000 |
| rxn concentrations | [asialo hSAP] rxn | μM | 24.1 |
| | max [Galactose] | μM | 241 |
| | [asialo hSAP] rxn | mg/mL | 2.8 |
| | [ST3Gal3] rxn | μM | 0.54 |
| | [ST3Gal3] rxn | mg/mL | 0.045 |
| | [CMP-SA] rxn | mM | 2.85 |
| | asialo hSAP:ST3 | mass ratio | 62 |
| | asialo hSAP:ST3 | molar ratio | 45 |
| | CMP-SA:ST3 | molar ratio | 5316 |
| | CMP-SA:asialo hSAP | molar ratio | 118 |
| | CMP-SA:Galactose | molar ratio | 11.8 |
| Treatment with α2,6 sialyltransferase (ST6 Rxn) | | | |
| hSAP, ST6 reagent stocks | [asialo hSAP] stk | mg/mL | 5.6 |
| | asialo hSAP MW | g/mol | 116293 |
| | [asialo hSAP] stk | μM | 48 |

| Asialo hSAP Rxns | | | | |
|---|---|---|---|---|
| | parameter | units | value | |
| | max [Galactose] | μM | 482 | |
| | [ST6] stk | mg/mL | 0.205 | |
| | ST6 MW | g/mol | 42000 | |
| | [ST6] stk | μM | 4.9 | |
| | [CMP-SA] stk | mg/mL | 25 | |
| | CMP-SA MW | g/mol | 658.4 | |
| | [CMP-SA] stk | mM | 38 | |
| rxn volumes | μL asialo hSAP in rxn | μL | 500 | |
| | μL ST6 in rxn | μL | 30 | |
| | μL CMP-SA in rxn | μL | 75 | |
| | buffer (10 mM HEPES/150 mM NaCl, pH 8) | μL | 395 | |
| | tot rxn vol | μL | 1000 | |
| rxn concentrations | [asialo hSAP] rxn | μM | 24.1 | |
| | max [Galactose] | μM | 241 | |
| | [asialo hSAP] rxn | mg/mL | 2.8 | |
| | [ST6] rxn | μM | 0.146 | |
| | [ST6] rxn | mg/mL | 0.006 | |
| | [CMP-SA] rxn | mM | 2.85 | |
| | asialo hSAP:ST6 | mass ratio | 455 | |
| | asialo hSAP:ST6 | molar ratio | 164 | |
| | CMP-SA:ST6 | molar ratio | 19448 | |
| | CMP-SA:asialo hSAP | molar ratio | 118 | |
| | CMP-SA:Galactose | molar ratio | 11.8 | |

In a separate reaction, complete sialylation of rhSAP using the α-2,3-sialyltransferase without first desialylating the molecule was preformed at 37° C. for 17 hours according to the following table.

| Treatment with α2,3 sialyltransferase (ST3Gal3) | | | | |
|---|---|---|---|---|
| | parameter | units | value | |
| rhSAP ST3Gal3 reagent stocks | [rhSAP] stk | mg/mL | 19.0 | |
| | rhSAP MW | g/mol | 116293 | |
| | [rhSAP] stk | μM | 163 | |
| | max [Galactose] | μM | 1634 | |
| | [ST3Gal3] stk | mg/mL | 0.9 | |
| | ST3Gal3 MW | g/mol | 84000 | |
| | [ST3Gal3] stk | μM | 10.7 | |
| | [CMP-SA] stk | mg/mL | 25 | |
| | CMP-SA MW | g/mol | 658.4 | |
| | [CMP-SA] stk | mM | 38 | |
| rxn volumes | μL rhSAP in rxn | μL | 500 | |
| | μL ST3Gal3 in rxn | μL | 50 | |
| | μL CMP-SA in rxn | μL | 100 | |
| | buffer (10 mM HEPES/150 mM NaCl, pH 8) | μL | 350 | |
| | tot rxn vol | μL | 1000 | |
| rxn concentrations | [rhSAP] rxn | μM | 81.7 | |
| | max [Galactose] | μM | 817 | |
| | [rhSAP] rxn | mg/mL | 9.5 | |
| | [ST3Gal3] rxn | μM | 0.54 | |
| | [ST3Gal3] rxn | mg/mL | 0.045 | |
| | [CMP-SA] rxn | mM | 3.80 | |
| | BTA-02-17:ST3 | mass ratio | 211 | |
| | BTA-02-17:ST3 | molar ratio | 152 | |
| | CMP-SA:ST3 | molar ratio | 7088 | |
| | CMP-SA:BTA-02-17 | molar ratio | 46 | |
| | CMP-SA:Galactose | molar ratio | 4.6 | |

After sialylation treatment, both sialylated rhSAP and hSAP variants were purified using PE affinity chromatography followed by dialysis into 10 mM NaPi/5% sorbitol pH 7.5 (P5S buffer). Confirmation of the desired sialic acid linkages (i.e, α-2,3-linked hSAP and α-2,6-linked RHSAP) was preformed using both Liquid Chromatography Mass Spectrometry (FIG. 2; A, C, and E) and Anion-Exchange High Performance Liquid Chromatography (FIG. 2; B, D, and F) following treatment of the glycovariant SAP polypeptides with α 2,3 sialidase (Calbiochem Cat#480706) at 37° C. for 24 hours.

Example 3

In Vitro Bioassays to Determine SAP Glycovariant Potency for Inhibiting Monocyte Differentiation into Fibrocytes Glycoremodeled rhSAP and hSAP were assayed for bioactivity using the same in vitro bioassay described in Example 1. In brief, monocyte enriched peripheral blood mononuclear cells (PBMCs) were incubated with varying concentrations of an SAP polypeptide for 96 hours. Following this incubation, resulting culture supernatants were removed and assayed by ELISA to quantify the about of Macrophage Derived Chemokine (MDC) that was produced. The results were expressed as an $IC_{50}$ ratio of the sample versus the hSAP reference standard and plotted as relative activity (relative activity of hSAP=1). All α-2,3-sialic acid linkage containing test materials are ≥2.4-fold more active than hSAP (FIG. 3). Equal mixtures of α-2,3- and α-2,6-linked sialic acid derivatives of SAP show intermediate activity levels between 100% α-2,6-linked and 100% α-2,3-linked SAP as expected (two rightmost bars in FIG. 3).

An alternative method of quantifying fibrocyte differentiation involves directly enumerating the number of fibrocytes that are generated after monocytes are incubated with a fibrocyte suppressant (e.g., SAP or variant thereof) or activating agent (e.g., M-CSF). In one experiment, monocytes were purified from whole blood-derived PBMC using negative magnetic bead selection standard in the art (e.g. CAT#113-41D, Invitrogen, Carlsbad, Calif.) and cultured in a 96-Well tissue culture plate containing FibroLife Media supplemented with 25 or 50 ng/ml of M-CSF in triplicate. The plate was incubated for 96 hours at 37° C. in a 5% $CO_2$ incubator. The cells were then fixed with paraformaldehyde and stained with Hema 3 stain (Cat #122-911, Hema 3 Stain, Fisher Scientific, Hampton, N.H.). The number of fibrocytes per well were determined by summing the count of five different fields per well using an inverted microscope. Fibrocytes were defined morphologically as adherent cells with an elongated spindle-shape and the presence of an oval nucleus. The data indicated that either 25 or 50 ng/ml of M-CSF was sufficient to increase the number of fibrocytes differentiating from monocytes by ~50% in this donor (FIG. 4). Subsequent experiments used FibroLife Media supplemented with 25 ng/ml of M-CSF as needed and defined below.

Fibrolife Media: (Cat # LM-0001, Lifeline Cell Technology, Walkersville, Md.) supplemented with 10 mM HEPES (Cat # H0887, Sigma-Aldrich), 1× non-essential amino acids (Cat # M7145, Sigma-Aldrich), 1 mM sodium pyruvate (Cat # S8636, Sigma-Aldrich), 2 mM glutamine (Cat #25030-149, Invitrogen), 100 U/ml penicillin and 100 ug/ml streptomycin (Cat # P0781, Sigma-Aldrich), and ITS-3 (Cat # I2771,500 ug/ml bovine serum albumin, 10 ug/ml insulin, 5 ug/ml transferrin, 5 ng/ml sodium selenite, 5 ug/ml linoleic acid, and 5 ug/ml oleic acid; Sigma-Aldrich).

In an additional experiment, PBMC or monocytes were purified from whole blood and cultured in FibroLife Media supplemented with various amounts of SAP in triplicate (as described above). The plate was incubated for 96 hours at 37° C. in a 5% $CO_2$ incubator. The cells were then fixed with paraformaldehyde and stained with Hema 3 stain (Cat #122-911, Hema 3 Stain, Fisher Scientific, Hampton, N.H.). The number of fibrocytes per well were determined by summing the count of five different fields per well using an inverted microscope. The minimum concentration of SAP necessary to provide maximum inhibition of fibrocyte differentiation in this system was determined to be 2 ug/ml (FIG. 5). The number of fibrocytes decreases with increasing SAP concentration in all donors.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will be apparent to those skilled in the art upon review of this specification and the below-listed claims. The full scope of the invention should be determined by reference to the claims, along with their full scope of equivalents, and the specification, along with such variations.

We claim:

1. A glycosylated human Serum Amyloid P (SAP) protein comprising an N-linked oligosaccharide chain, wherein at least one branch of the N-linked oligosaccharide chain terminates with an α2,3-linked sialic acid moiety, wherein the SAP protein comprises a polypeptide comprising the amino acid sequence of SEQ ID NO: 1 or variant thereof, and wherein the SAP protein inhibits the differentiation of monocytes into fibrocytes in vitro.

2. The glycosylated human SAP protein of claim 1, wherein the N-linked oligosaccharide chain has at least 50% fewer α2,6-linked sialic acid moieties than a wild-type SAP protein isolated from human serum.

3. The glycosylated human SAP protein of claim 1, wherein all branches of the N-linked oligosaccharide chain terminate with α2,3-linked sialic acid moieties.

4. The glycosylated human SAP protein of claim 1, wherein the N-linked oligosaccharide chain is substantially free of α2,6-linked sialic acid moieties.

5. The glycosylated human SAP protein of claim 1, wherein the protein comprises a polypeptide comprising an amino acid sequence that is at least 95% identical to the amino acid sequence of SEQ ID NO: 1.

6. The glycosylated human SAP protein of claim 1, wherein the protein is a fusion protein comprising an SAP domain and one or more heterologous domains.

7. The glycosylated human SAP protein of claim 1, wherein the protein comprises one or more modified amino acid residues.

8. The glycosylated human SAP protein of claim 7, wherein the one or more modified amino acid residues comprise: a PEGylated amino acid, a prenylated amino acid, an acetylated amino acid, a biotinylated amino acid, or an amino acid conjugated to an organic derivatizing agent.

9. The glycosylated human SAP protein of claim 1, wherein the SAP protein has an $IC_{50}$ for inhibiting the differentiation of monocytes into fibrocytes in vitro that is less than one-half that of a corresponding sample of a wild-type SAP protein isolated from human serum.

10. A pharmaceutical preparation suitable for use in a mammal comprising the glycosylated human SAP protein of claim 1 and a pharmaceutically acceptable carrier.

11. A method of treating fibrosis in a patient, the method comprising administering to a patient in need thereof a therapeutically effective amount of the glycosylated human SAP protein of claim 1.

12. A method of making a human SAP protein comprising an N-linked oligosaccharide chain, wherein at least one branch of the oligosaccharide chain terminates with an α2,3-linked sialic acid moiety, the method comprising:
  i) expressing a human SAP protein in a CHO cell; and
  ii) isolating the human SAP protein from the cell, wherein the isolated human SAP protein comprises an N-linked oligosaccharide chain, and wherein at least one branch of the N-linked oligosaccharide chain terminates with an α2,3-linked sialic acid moiety.

13. The method of claim 12, wherein the N-linked oligosaccharide chain has at least 50% fewer α2,6-linked sialic acid moieties than a wild-type SAP protein isolated from human serum.

14. The method of claim 12, wherein the isolated human SAP protein has an $IC_{50}$ for inhibiting the differentiation of monocytes into fibrocytes in vitro that is less than one-half that of a corresponding sample of a wild-type SAP protein isolated from human serum.

15. The method of claim 12, further comprising enzymatically or chemically altering the isolated SAP protein to produce an SAP protein having a modified oligosaccharide chain.

16. The method of claim 15, wherein the process of enzymatically or chemically altering the isolated SAP protein removes one or more terminal α2,6-linked sialic acid moieties from the oligosaccharide chain.

17. The method of claim 15, wherein the process of enzymatically or chemically altering the isolated SAP protein replaces one or more terminal α2,6-linked sialic acid moieties on the oligosaccharide chain with one or more α2,3-linked sialic acid moieties.

18. A method of making an SAP protein, comprising:
  i) providing an SAP protein; and
  ii) enzymatically or chemically altering the SAP protein to produce a glycosylated SAP protein comprising an N-linked oligosaccharide, wherein at least one branch of the N-linked oligosaccharide chain terminates with an α2,3-linked sialic acid moiety.

19. The method of claim 18, wherein the N-linked oligosaccharide chain has at least 50% fewer α2,6-linked sialic acid moieties than a wild-type human SAP protein isolated from human serum.

20. The method of claim 18, wherein the glycosylated SAP protein has an $IC_{50}$ for inhibiting the differentiation of monocytes into fibrocytes in vitro that is less than one-half that of a corresponding sample wild-type SAP protein isolated from human serum.

21. The glycosylated human SAP protein of claim 1, wherein the protein comprises a polypeptide comprising the amino acid sequence of SEQ ID NO: 1.

22. A method of treating mucositis in a patient, the method comprising administering to a patient in need thereof a therapeutically effective amount of the glycosylated human SAP protein of claim 1.

23. The glycosylated human SAP protein of claim 1, wherein the protein comprises a polypeptide comprising an amino acid sequence that is at least 98% identical to the amino acid sequence of SEQ ID NO: 1.

24. The method of claim 12, wherein the N-linked oligosaccharide chain is substantially free of α2,6-linked sialic acid moieties.

25. The method of claim 12, wherein all branches of the N-linked oligosaccharide chain terminate with α2,3-linked sialic acid moieties.

26. The method of claim 18, wherein the N-linked oligosaccharide chain is substantially free of α2,6-linked sialic acid moieties.

27. The method of claim 18, wherein all branches of the N-linked oligosaccharide chain terminate with α2,3-linked sialic acid moieties.

28. The pharmaceutical preparation of claim 10, wherein the pharmaceutical preparation is suitable for administration to a patient topically, by injection, by intravenous injection, by inhalation, by continuous depot, or by pump.

29. The method of claim 11, wherein the N-linked oligosaccharide chain has at least 50% fewer α2,6-linked sialic acid moieties than a wild-type SAP protein isolated from human serum.

30. The method of claim 11, wherein all branches of the N-linked oligosaccharide chain terminate with α2,3-linked sialic acid moieties.

31. The method of claim 11, wherein the N-linked oligosaccharide chain is substantially free of α2,6-linked sialic acid moieties.

32. The method of claim 11, wherein the SAP protein comprises a polypeptide comprising an amino acid sequence that is at least 95% identical to the amino acid sequence of SEQ ID NO: 1.

33. The method of claim 11, where the SAP protein comprises a polypeptide comprising the amino acid sequence of SEQ ID NO: 1.

34. The method of claim 11, wherein the SAP protein has an $IC_{50}$ for inhibiting the differentiation of monocytes into fibrocytes in vitro that is less than one-half that of a corresponding sample of a wild-type SAP protein isolated from human serum.

35. The method of claim 22, wherein the N-linked oligosaccharide chain has at least 50% fewer α2,6-linked sialic acid moieties than a wild-type SAP protein isolated from human serum.

36. The method of claim 22, wherein all branches of the N-linked oligosaccharide chain terminate with α2,3-linked sialic acid moieties.

37. The method of claim 22, wherein the N-linked oligosaccharide chain is substantially free of α2,6-linked sialic acid moieties.

38. The method of claim 22, wherein the SAP protein comprises a polypeptide comprising an amino acid sequence that is at least 95% identical to the amino acid sequence of SEQ ID NO: 1.

39. The method of claim 22, where the SAP protein comprises a polypeptide comprising the amino acid sequence of SEQ ID NO: 1.

40. The method of claim 22, wherein the SAP protein has an $IC_{50}$ for inhibiting the differentiation of monocytes into fibrocytes in vitro that is less than one-half that of a corresponding sample of a wild-type SAP protein isolated from human serum.

41. The method of claim of claim 12, wherein the CHO cell is a CHO—S cell.

42. The glycosylated human SAP protein of claim 1, wherein all sialylated branches of the N-linked oligosaccharide chain terminate with α2,3-linked sialic acid moieties.

43. The method of claim 12, wherein all sialylated branches of the N-linked oligosaccharide chain terminate with α2,3-linked sialic acid moieties.

44. The method of claim 18, wherein all sialylated branches of the N-linked oligosaccharide chain terminate with α2,3-linked sialic acid moieties.

45. The pharmaceutical composition of claim 10, wherein the glycosylated human SAP protein is substantially free of α2,6-linked sialic acid moieties.

46. The glycosylated human SAP protein of claim 2, wherein the SAP protein has an $IC_{50}$ for inhibiting the differentiation of monocytes into fibrocytes in vitro that is less than one-half that of a corresponding sample of a wild-type SAP protein isolated from human serum.

47. The glycosylated human SAP protein of claim 4, wherein the SAP protein has an $IC_{50}$ for inhibiting the differentiation of monocytes into fibrocytes in vitro that is less than one-half that of a corresponding sample of a wild-type SAP protein isolated from human serum.

48. The glycosylated human SAP protein of claim 1, wherein the glycosylated human SAP protein has at least 85% fewer α2,6-linked sialic acid moieties than a wild-type SAP protein isolated from human serum.

49. The glycosylated human SAP protein of claim 1, wherein the glycosylated human SAP protein is a recombinant human SAP protein.

50. The method of claim 11, wherein all sialylated branches of the N-linked oligosaccharide chain terminate with α2,3-linked sialic acid moieties.

51. The method of claim 22, wherein all sialylated branches of the N-linked oligosaccharide chain terminate with α2,3-linked sialic acid moieties.

52. A glycosylated human Serum Amyloid P (SAP) protein comprising an N-linked oligosaccharide chain, wherein at least one branch of the N-linked oligosaccharide chain terminates with an α2,3-linked sialic acid moiety, and wherein the SAP protein has fewer α2,6-linked sialic acid moieties than naturally occurring human SAP from human serum, wherein the SAP protein comprises a polypeptide comprising the amino acid sequence of SEQ ID NO: 1 or variant thereof, and wherein the SAP protein inhibits the differentiation of monocytes into fibrocytes in vitro.

* * * * *